(12) United States Patent
Yokoyama et al.

(10) Patent No.: US 7,869,568 B2
(45) Date of Patent: Jan. 11, 2011

(54) RADIATION IMAGING APPARATUS, AND METHOD AND PROGRAM FOR CONTROLLING RADIATION IMAGING APPARATUS

(75) Inventors: Keigo Yokoyama, Honjo (JP); Tadao Endo, Honjo (JP); Toshio Kameshima, Kumagaya (JP); Tomoyuki Yagi, Honjo (JP); Katsuro Takenaka, Honjo (JP)

(73) Assignee: Canon Kabushiki Kaisha, Tokyo (JP)

( * ) Notice: Subject to any disclaimer, the term of this patent is extended or adjusted under 35 U.S.C. 154(b) by 232 days.

(21) Appl. No.: 12/039,983

(22) Filed: Feb. 29, 2008

(65) Prior Publication Data

US 2008/0226031 A1     Sep. 18, 2008

(30) Foreign Application Priority Data

Mar. 13, 2007  (JP)  ............................. 2007-064124
Feb. 13, 2008  (JP)  ............................. 2008-032200

(51) Int. Cl.
    *H05G 1/64*    (2006.01)
(52) U.S. Cl. ..................................... 378/98.8; 378/207
(58) Field of Classification Search ................ 378/98.8, 378/114, 115, 207; 250/252.1, 370.09
    See application file for complete search history.

(56) References Cited

U.S. PATENT DOCUMENTS

| | | | | |
|---|---|---|---|---|
| 5,905,772 A | 5/1999 | Rutten et al. | ................ | 378/98.8 |
| 6,859,521 B2 * | 2/2005 | Spahn | ......................... | 378/117 |
| 6,952,015 B2 | 10/2005 | Kameshima | ............ | 250/370.11 |
| 6,952,464 B2 | 10/2005 | Endo | ........................ | 378/98.11 |
| 6,965,111 B2 | 11/2005 | Endo | ........................ | 250/370.11 |
| 6,985,556 B2 * | 1/2006 | Shanmugavel et al. | ....... | 378/117 |
| 7,012,260 B2 | 3/2006 | Endo | ........................ | 250/370.11 |
| 7,227,926 B2 | 6/2007 | Kameshima et al. | ........ | 378/98.9 |
| 7,342,221 B2 | 3/2008 | Takenaka et al. | ........... | 250/252.1 |
| 2005/0199834 A1 | 9/2005 | Takenaka et al. | ............. | 250/580 |
| 2005/0200720 A1 | 9/2005 | Kameshima et al. | ...... | 348/220.1 |
| 2005/0220269 A1 | 10/2005 | Endo et al. | ................... | 378/114 |
| 2005/0264665 A1 | 12/2005 | Endo et al. | ................... | 348/308 |
| 2006/0119719 A1 | 6/2006 | Kameshima | ................ | 348/308 |
| 2006/0192130 A1 | 8/2006 | Yagi | ....................... | 250/370.14 |
| 2006/0289774 A1 | 12/2006 | Endo et al. | ............. | 250/370.09 |
| 2007/0040099 A1 | 2/2007 | Yokoyama et al. | ........ | 250/208.1 |
| 2007/0080299 A1 | 4/2007 | Endo et al. | ............. | 250/370.09 |
| 2007/0096032 A1 | 5/2007 | Yagi et al. | .............. | 250/370.11 |
| 2007/0125952 A1 | 6/2007 | Endo et al. | ................... | 250/369 |
| 2007/0131843 A1 | 6/2007 | Yokoyama et al. | ........... | 250/205 |
| 2007/0210258 A1 | 9/2007 | Endo et al. | ............. | 250/370.09 |
| 2007/0290143 A1 | 12/2007 | Kameshima et al. | ... | 250/370.09 |
| 2007/0291904 A1 | 12/2007 | Takenaka et al. | ............. | 378/207 |

(Continued)

*Primary Examiner*—Chih-Cheng G Kao
(74) *Attorney, Agent, or Firm*—Fitzpatrick, Cella, Harper & Scinto

(57) ABSTRACT

A radiation imaging apparatus is provided that stabilizes a dark current, image ghosting, and the sensitivity of the imaging apparatus, reduces the power consumption and the heat generation of a light source, and improves the durability of a conversion element. The radiation imaging apparatus includes a flat panel detector including a conversion unit, where the conversion unit includes a plurality of pixels arranged in a matrix and each of the pixels includes a conversion element capable of converting a radiation ray into electric charge, a light source capable of emitting light to the conversion unit, and a control unit configured to control the flat panel detector and the light source. The control unit controls the emission of light performed by the light source on the basis of a signal output from the flat panel detector.

12 Claims, 17 Drawing Sheets

U.S. PATENT DOCUMENTS

| | | |
|---|---|---|
| 2007/0297567 A1 | 12/2007 | Takenaka et al. ............ 378/98.2 |
| 2008/0011958 A1 | 1/2008 | Endo et al. ............. 250/370.08 |
| 2008/0013686 A1 | 1/2008 | Kameshima et al. .......... 378/98 |
| 2008/0029688 A1 | 2/2008 | Yagi et al. ................. 250/208.1 |
| 2008/0054182 A1 | 3/2008 | Yokoyama et al. ..... 250/370.09 |
| 2008/0083876 A1 | 4/2008 | Endo et al. ................... 250/369 |

* cited by examiner

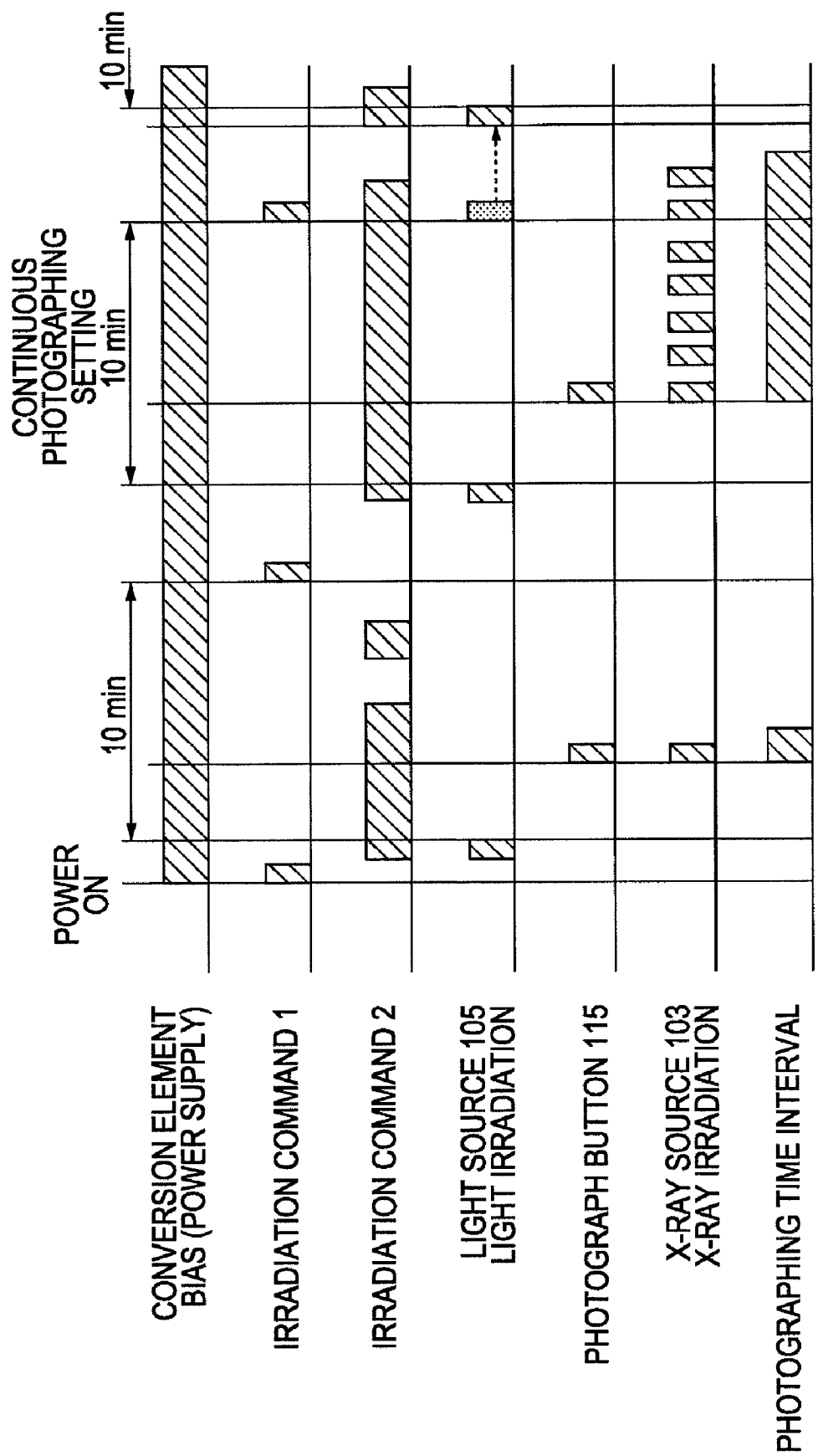

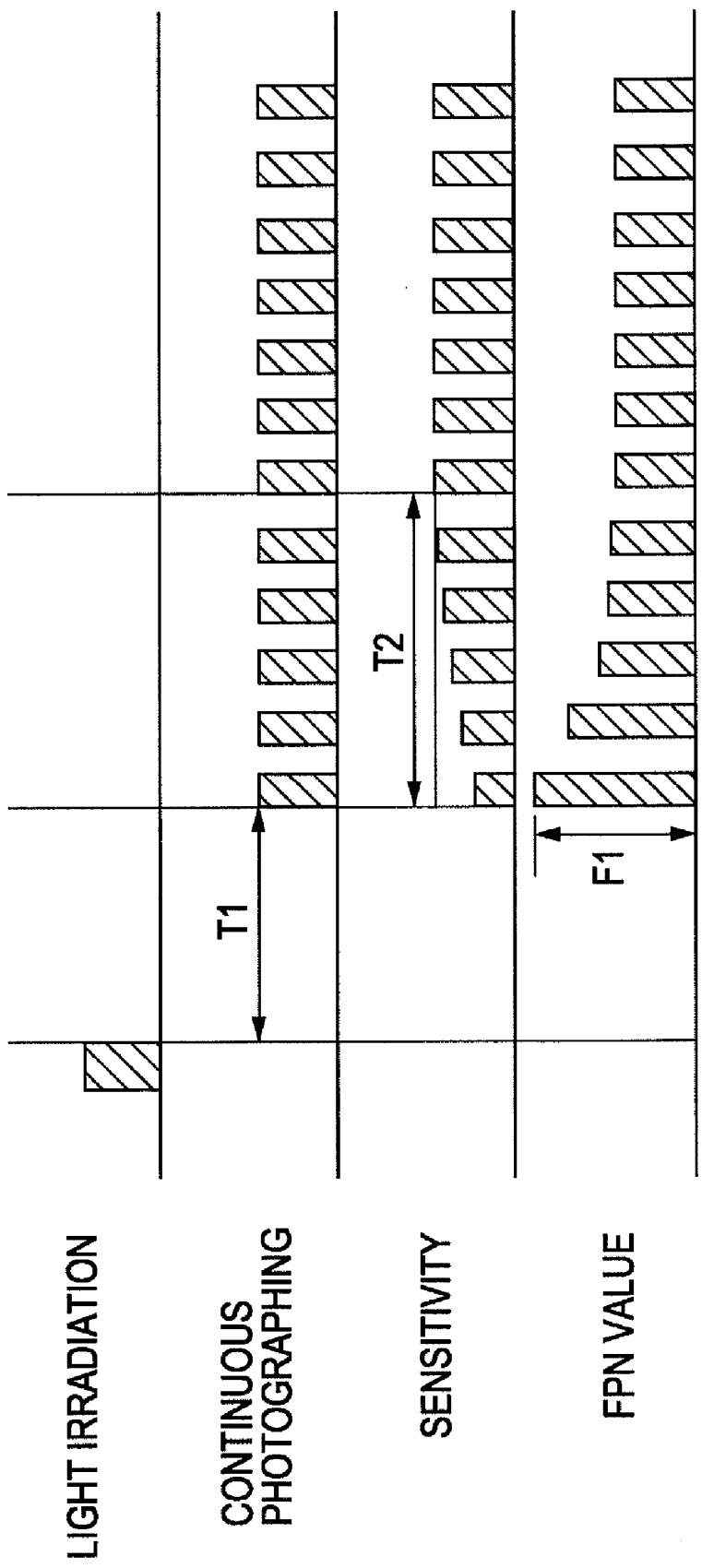

RADIATION IMAGING APPARATUS, AND METHOD AND PROGRAM FOR CONTROLLING RADIATION IMAGING APPARATUS

BACKGROUND OF THE INVENTION

1. Field of the Invention

The present invention relates to a radiation imaging apparatus and radiation imaging system that are suitable for use in medical diagnostics and industrial nondestructive inspection. As used herein, the term "radiation" refers to electromagnetic waves including X-rays and γ rays and radiation rays including α rays and β rays.

2. Description of the Related Art

In recent years, digital radiation imaging apparatuses including a conversion element that converts a radiation ray or a light ray into electric charge and are made from a non-single crystal semiconductor, such as amorphous silicon or amorphous selenium, have been commercially available. In addition, digital radiation imaging apparatuses including a photoelectric conversion element that converts a radiation ray or a light ray to electric charge and which are made from a single crystal semiconductor, such as a charged-coupled device (CCD) or a complementary metal-oxide semiconductor (CMOS), have been commercially available. Some radiation imaging apparatuses employ an indirect method. In the indirect method, a conversion element includes a phosphor that converts a radiation ray to a visible light ray and a photoelectric conversion element that converts the visible light ray to electric charge. The photoelectric conversion element is primarily made of amorphous silicon. In contrast, some radiation imaging apparatuses employ a direct method. In the direct method, a conversion element is primarily made of amorphous selenium, and directly converts a radiation light ray to electric charge. In both methods, radiation imaging apparatuses having large dimensions and a thin shape can be achieved. Accordingly, such radiation imaging apparatuses are also referred to as "flat panel detectors (FDPs)". Such radiation imaging apparatuses can significantly reduce the period of time from when an image is captured until an observer can view the image.

These radiation imaging apparatuses may be influenced by the time elapsed from when the apparatuses are powered on and a bias is provided to the conversion element, a period of time during an image capturing operation, and an amount of radiation reaching the apparatuses. Accordingly, the characteristics of the radiation imaging apparatuses may vary, and therefore, an image signal acquired by the radiation imaging apparatuses may vary. For example, the dangling bond or defects of the conversion element functions as a trap level, so that a dark current varies. Alternatively, image ghosting (a lag) may occur or vary due to the influence of past radiation or past light irradiation. In addition, due to at least one of the above, the sensitivity of the conversion element that defines an input and output characteristic between the input of radiation or light and the output of electric charge may vary.

Accordingly, for example, U.S. Pat. Nos. 6,965,111 and 5,905,772 describe a technology in which, before a radiation ray or a light ray used for acquiring a subject image is emitted to a radiation imaging apparatus, a light ray not used for acquiring the subject image is emitted from another light source. In this way, variations in the characteristics of the apparatus and variation in an acquired image signal can be reduced.

SUMMARY OF THE INVENTION

However, if, as described in U.S. Pat. Nos. 6,965,111 and 5,905,772, as the period of time from when a light ray having no subject information is emitted until a photographing operation is performed increases, the above-described effect of reducing the variations is disadvantageously lowered.

In addition, if the amount of the light ray having no subject information is increased or the number of the light emissions is increased, the amount of an electrical current flowing in a light source that emits the light ray increases. Accordingly, the load of the light source disadvantageously increases. In addition, as the amount of electrical current increases, power consumption of the light source increases. Furthermore, the heat generation of the light source increases.

Furthermore, if the amount of the light ray emitted from a light source is increased or the number of the light emissions is increased, the performance of a conversion element exposed to the light deteriorates.

The present invention provides a radiation imaging apparatus that stabilizes a dark current, image ghosting, and the sensitivity of an imaging unit, that reduces the power consumption and heat generation of the light source, and that reduces the deterioration of the performance of the conversion element.

According to an embodiment of the present invention, a radiation imaging apparatus includes a flat panel detector including a conversion unit, where the conversion unit includes a plurality of pixels arranged in a matrix, each of the pixels including a conversion element capable of converting a radiation ray into electric charge, a light source capable of emitting light to the conversion unit, and a control unit configured to control the flat panel detector and the light source. The control unit controls the emission of light emitted by the light source on the basis of a signal output from the flat panel detector.

According to another embodiment of the present invention, a method for controlling a radiation imaging apparatus is provided. The method includes the steps of receiving a signal from a flat panel detector including a conversion unit, where the conversion unit includes a plurality of pixels arranged in a matrix, each of the pixels including a conversion element capable of converting a radiation ray into electric charge, and controlling a light source to emit light to the conversion unit on the basis of the received signal.

According to still another embodiment of the present invention, a program for causing a computer to control a radiation imaging apparatus is provided. The program includes program code for causing the radiation imaging apparatus to execute the step of receiving a signal from a flat panel detector including a conversion unit, where the conversion unit includes a plurality of pixels arranged in a matrix and each of the pixels includes a conversion element capable of converting a radiation ray into electric charge, and the step of controlling a light source to emit light to the conversion unit on the basis of the received signal.

According to the present invention, a dark current, image ghosting, and the sensitivity of an imaging unit can be stabilized. In addition, the load, power consumption, and heat generation of the light source can be reduced. Furthermore, deterioration of the performance of the conversion element can be reduced.

Further features of the present invention will become apparent from the following description of exemplary embodiments with reference to the attached drawings.

BRIEF DESCRIPTION OF THE DRAWINGS

FIG. 9 is a timing diagram of the operations performed by the radiation imaging apparatus and the radiation imaging system during a photographing operation of a subject according to the third embodiment of the present invention.

FIG. 14A is a timing diagram of the operations of a radiation imaging system in an experiment.

DESCRIPTION OF THE EMBODIMENTS

First Embodiment

Figure 1:
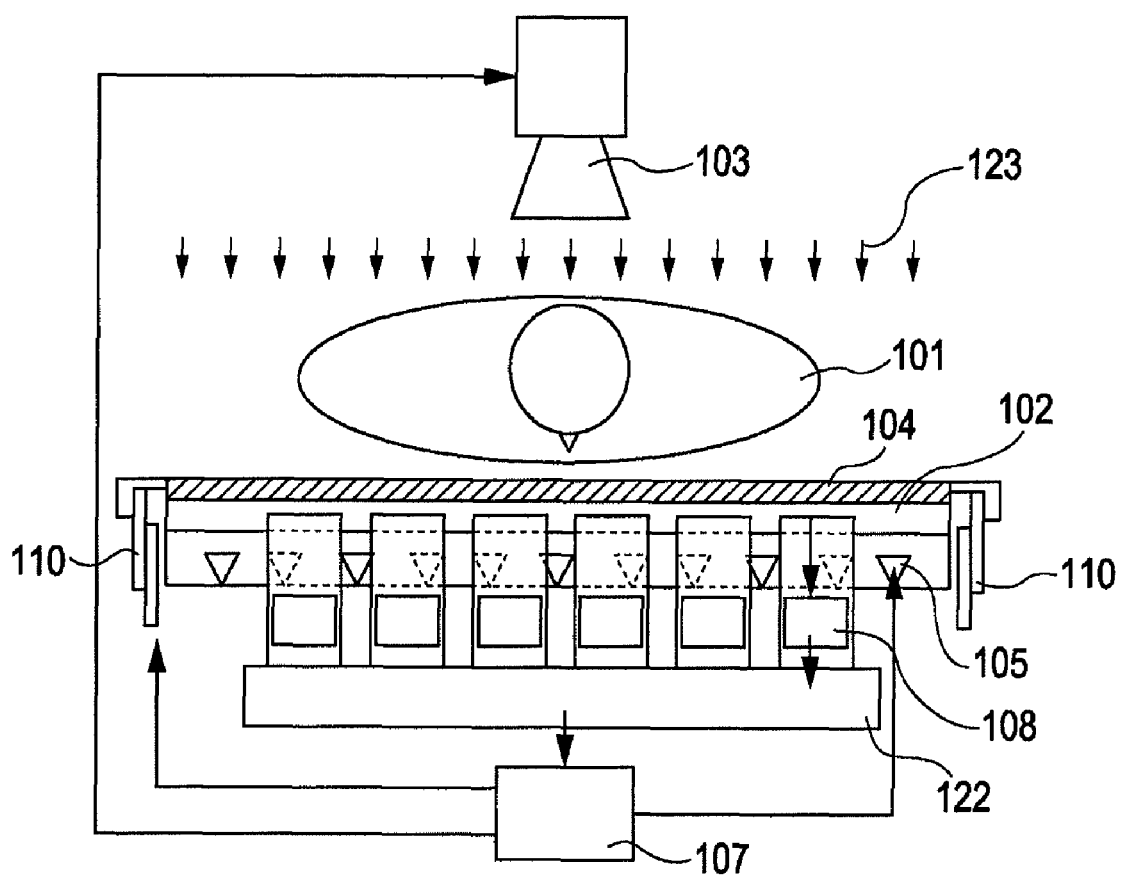
FIG. 1 is a schematic illustration of an exemplary configuration of a radiation imaging system according to a first embodiment of the present invention.

Components and functions of a radiation imaging apparatus according to a first embodiment of the present invention are described below with reference to the accompanying drawings. FIG. 1 is a schematic illustration of an exemplary configuration of a radiation imaging system according to the first embodiment of the present invention. According to the first embodiment, the radiation imaging system is primarily used for a medical purpose. A flat panel detector according to the present invention includes a wavelength converter 104 that converts the wavelength of a radiation ray, such as an X-ray, so that the radiation ray is converted to a visible light ray. The flat panel detector further includes a sensor panel 102 that outputs an electrical signal in accordance with an amount of the visible light ray. The flat panel detector further includes a drive circuit 110 that drives the sensor panel 102 and a readout circuit 108 that reads out the electrical signal from the sensor panel 102 and outputs a digital image signal. According to the present embodiment, the radiation imaging apparatus includes a light source 105. The light source 105 is made to emit light having no subject information onto the sensor panel 102 in order to reduce variations in the characteristics of the apparatus and an acquired image signal. According to the present embodiment, the radiation imaging apparatus includes at least the flat panel detector and the light source 105 in a housing (not shown). The radiation imaging system includes at least a radiation source 103 that emits a radiation ray and the radiation imaging apparatus that acquires a digital image signal based on an electrical signal in accordance with an amount of an emitted radiation ray. The radiation imaging system further includes an image processing circuit 122 that performs image processing on the acquired digital image signal as needed and a control unit 107 that controls the radiation source 103, the drive circuit 110, and the readout circuit 108. Note that, in order to perform image processing on a digital image signal, the image processing circuit 122 can employ any method that can solve the above-described problem.

The control unit 107 receives the digital image signal subjected to the image processing performed by the image processing circuit 122, and controls the operation of the light source 105 on the basis of the received digital image signal. At least one of the image processing circuit 122 and the control unit 107 may be incorporated in an integrated circuit (IC) that includes the readout circuit 108 or an IC that does not include the readout circuit 108. The IC may be disposed in the housing of the radiation imaging apparatus. The radiation imaging apparatus is installed so that a subject 101 is located between the radiation imaging apparatus and the radiation source 103. Thus, a digital image signal can be acquired on the basis of an electrical signal in accordance with an amount of a radiation ray that has passed through the subject 101 and that contains subject information.

According to the present embodiment, the indirect method is employed in which the wavelength converter 104 is provided and the sensor panel 102 converts a visible light ray having a wavelength converted from a radiation ray by the wavelength converter 104 into an electrical signal. However, the present invention is not limited thereto. For example, the direct method may be employed in which the sensor panel 102 directly converts a radiation ray into an electrical signal without using the wavelength converter 104.

According to the present invention, the operation of the light source 105 is controlled by the control unit 107. The control operation performed by the control unit 107 is described in more detail below. According to the first embodiment, the radiation imaging apparatus, the image processing circuit 122, and the control unit 107 function as a unit that detects information indicating whether or not light irradiation from the light source 105 to the sensor panel 102 is needed.

Figure 2:
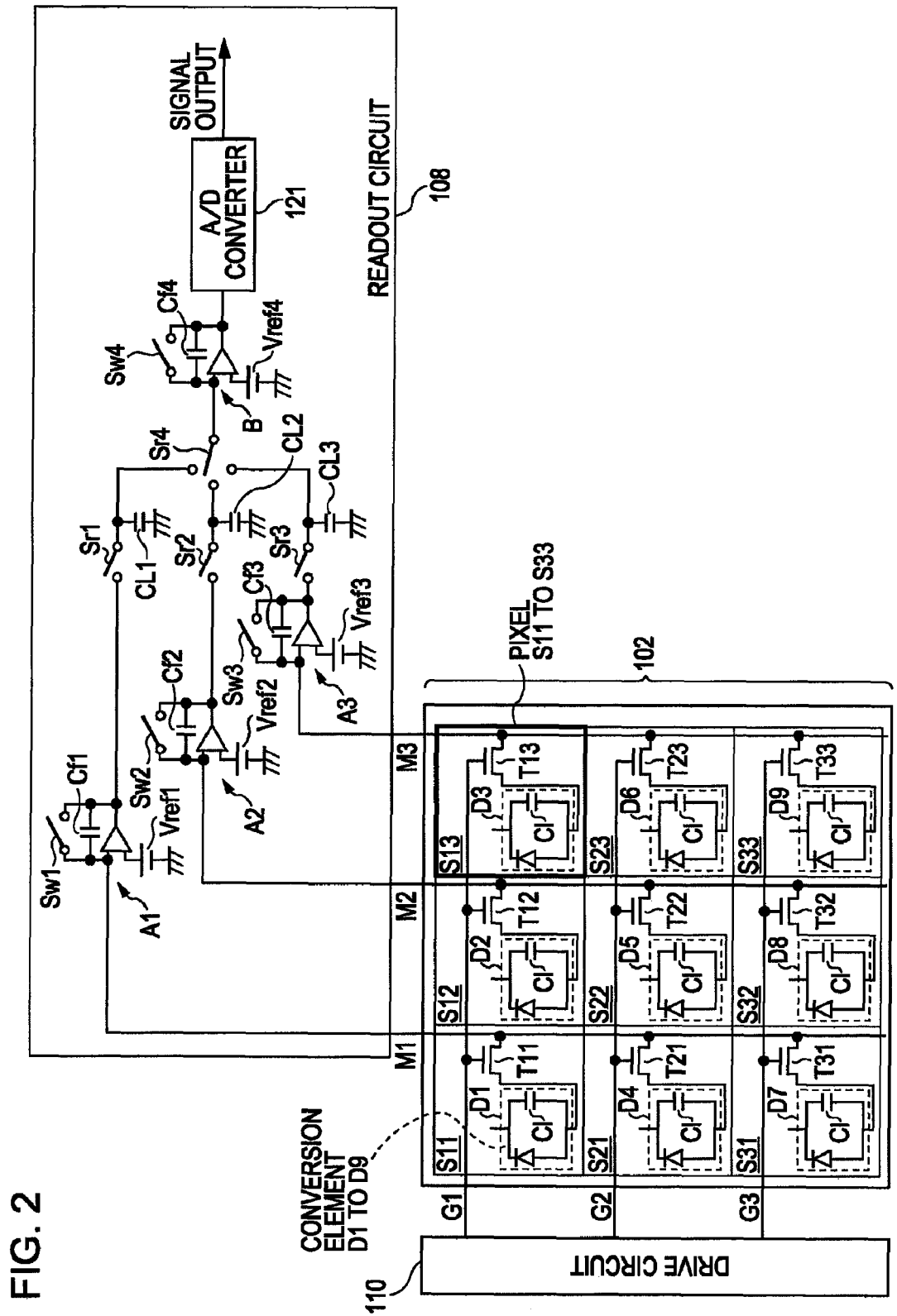
FIG. 2 is a circuit diagram illustrating an exemplary configuration of a radiation imaging apparatus according to the present invention.

The radiation imaging apparatus according to the present embodiment is described in detail next with reference to FIG. 2. FIG. 2 is a circuit diagram illustrating an exemplary configuration of the radiation imaging apparatus according to the present embodiment. For simplicity, in FIG. 2, the number of pixels is nine (three rows and three columns). However, the present invention is not limited thereto. The number of pixels (the size of a pixel array) can be appropriately determined as needed.

According to the present embodiment, the sensor panel 102 of the radiation imaging apparatus includes a conversion unit. The conversion unit includes pixels S11 to S33 disposed on an insulating substrate, such as a glass substrate, in a matrix. The pixels S11 to S33 include conversion elements D1 to D9 that convert a radiation ray or a light ray into electric charge and switching elements T11 to T33 that output electrical signals based on the converted electric charge, respectively. A capacitance element C1 that accumulates the detected electric charge is provided inside or outside each of the conversion elements D1 to D9.

According to the present embodiment, each of the conversion elements D1 to D9 includes a wavelength converter (not shown) and a photoelectric conversion element. The wavelength converter converts a radiation ray into a light ray detectable by the photoelectric conversion element. The photoelectric conversion element converts the light ray into electric charge. The wavelength converter can be made from CsI:Tl or $Gd_2O_2S$:Tb. The photoelectric conversion element can be an MIS photoelectric conversion element made from amorphous silicon. However, the present invention is not limited thereto. For example, a PIN photodiode can be used. In addition, an element that is primarily made from amorphous selenium and that can directly convert a radiation ray into electric charge can be used for each of the conversion elements D1 to D9. Each of the conversion elements D1 to D9 includes at least two electrodes and a semiconductor layer disposed between the two electrodes.

According to the present embodiment, a thin film transistor (TFT) primarily made from amorphous silicon is used for each of the switching elements T11 to T33. However, the present invention is not limited thereto. For example, a TFT primarily made from polysilicon may be used. In addition, according to the present embodiment, a three-terminal active element is used. However, the present invention is not limited thereto. For example, a two-terminal active element, such as a switching diode, may be used.

In addition, according to the present embodiment, one of two electrodes of the conversion element is connected to one of the source and the drain of the switching element, which are main electrodes of the switching element. However, the present invention is not limited thereto. For example, the conversion element may be connected to the gate of the switching element so that a source follower amplifier is formed. In such a case, an additional switching element may be provided in order to initialize the potential of a connection point between the conversion element and the gate of the switching element.

Drive wires G1 to G3 are connected to the gates of the switching elements of a plurality of pixels arranged in the corresponding rows. The drive wires G1 to G3 transmit drive signals output from the drive circuit 110 to the switching elements. Signal wires M1 to M3 are connected to the other of the source and the drain of each of the switching elements of the plurality of pixels arranged in the corresponding columns. The signal wires M1 to M3 transmit electrical signals output from the switching elements to the readout circuit 108. In addition, a bias wire (not shown) is connected to the other electrode of the conversion element of each of the pixels. Thus, a bias required for converting the radiation ray or a light ray into electric charge is provided to each of the conversion elements. The sensor panel 102 includes the pixels S11 to S33 disposed on the insulating substrate, the drive wires G1 to G3, the signal wires M1 to M3, and the bias wire.

The drive circuit 110 is electrically connected to the drive wires G1 to G3. The drive circuit 110 applies, using the drive wires G1 to G3, a drive signal to the switching elements of the plurality of pixels connected to the drive wires G1 to G3 on a row-to-row basis. In this way, the drive circuit 110 controls the states of the switching elements between a conductive state and a non-conductive state. Thus, the drive circuit 110 drives the sensor panel 102. The drive signal output from the drive circuit 110 includes a pulse conductive voltage that switches the switching element to a conductive state. For example, when a drive signal is applied to switching elements T11 to T13 via the drive wire G1 for a first row, the switching elements T11 to T13 enter a conductive state. The switching elements T11 to T13 simultaneously output electrical signals in accordance with electric charge of the conversion elements D1 to D3 to the signal wires M1 to M3, respectively, on a row-to-row basis. In the same manner, the switching elements arranged in the second row and the switching elements arranged in the third row are sequentially driven. The electrical signals output from the pixels on a row-to-row basis are converted into a digital image signal for a frame by the readout circuit 108. Thereafter, the digital image signal is output.

The readout circuit 108 is electrically connected to the signal wires M1 to M3. The readout circuit 108 simultaneously reads out electrical signals output on a row-to-row basis via the signal wires M1 to M3. The readout circuit 108 converts these parallel signals into a serial signal. At the same time, the readout circuit 108 converts the signals from an analog format to a digital format. Thus, a digital image signal is output. The readout circuit 108 includes operational amplifiers A1 to A3 and sample and hold circuits. The operational amplifiers A1 to A3 are connected to the signal wires. The operational amplifiers A1 to A3 amplify the electrical signals input from the signal wires and output the amplified signals. The sample and hold circuits sample and hold the electrical signals output from the operational amplifiers A1 to A3. The sample and hold circuits include switch Sr1 to Sr3 that sample the electrical signals and capacitors CL1 to CL3 that hold the sampled electrical signal. The operational amplifier (one of the operational amplifiers A1 to A3) and the sample and hold circuit are provided for each of the signal wires M1 to M3. The electrical signals output in parallel are processed in parallel until the electrical signals reach the sample and hold circuits.

The readout circuit 108 further includes a multiplexer Sr4 and an amplifier B. The multiplexer Sr4 sequentially outputs the electrical signals held by the sample and hold circuits provided for the signal wires M1 to M3, and converts the electrical signals into a serial image signal. The amplifier B performs impedance transformation on the image signal output from the multiplexer. The readout circuit 108 further includes an analog-to-digital (A/D) converter 121 that converts the analog image signal output from the amplifier B to a digital image signal.

According to the present embodiment, the A/D converter 121 is disposed downstream of the multiplexer Sr4. However, the present invention is not limited thereto. For example, an A/D converter may be disposed upstream of the multiplexer Sr4 for each of the signal wires M1 to M3. In addition, the above-described configuration of the readout circuit 108 is only an example. The readout circuit 108 can have one of a variety of configurations that can receive analog signals from the signal wires M1 to M3, perform an amplifying operation, multiplexing, and an A/D conversion so that a digital image signal is output.

Although not shown in FIG. 2, the light source 105 is disposed between a surface (back surface) of the sensor panel 102 opposite the light receiving surface and the housing. Here, the pixels are formed on the light receiving surface of the sensor panel 102. The light receiving surface faces the wavelength converter 104. During a photographing operation, the receiving surface is irradiated with a radiation ray. An organic electroluminescence (EL) panel, a light emitting diode (LED), or a cold cathode ray tube is suitably used for the light source 105. In addition, a combination of one of these materials and an existing light guiding member may be used for the light source 105. It is desirable that the wavelength of a light ray emitted from the light source 105 is in the range that can be absorbed by the conversion elements D1 to D3. A light ray emitted from the light source 105 directly enters the back surface of the sensor panel 102 and is absorbed by the semiconductor layers of the conversion elements D1 to D3.

An exemplary image acquiring operation performed by the radiation imaging apparatus is described next with reference to FIG. 2. A radiation ray is emitted from a radiation source and passes through a subject. The radiation imaging apparatus is then irradiated with the radiation ray. The irradiated radiation ray is converted into a light ray having a wavelength within a wavelength range that is appropriate for the conversion elements D1 to D9 by the wavelength converter 104. The wavelength-converted light is emitted to the conversion elements D1 to D9. The conversion elements D1 to D9 generate electric charge in accordance with an amount of the emitted light. The generated electric charge is accumulated in the capacitance element C1. The above-described series of operations is referred to as an "accumulating operation".

Subsequently, drive signals are provided from the drive circuit 110 to the drive wires G1 to G3 so that the switching elements T11 to T33 are switched to a conductive state. Thus, a readout operation in which an electrical signal based on an electric charge is output from the pixel is performed. According to the present embodiment, the drive signals output from the drive circuit 110 are sequentially applied to the drive wire G1 for the first row, the drive wire G2 for the second row, and the drive wire G3 for the third row. That is, in order to perform a readout operation, the switching elements are controlled on a row-to-row basis so that the electrical signals are simultaneously output from the pixels on a row-to-row basis. A drive signal is applied from the drive circuit 110 to the drive wire G1 for the first row first. Thus, a conductive voltage is applied to control terminals of the switching elements T11 to T13 for the first row. Consequently, the switching elements T11 to T13 for the first row turn on. The electrical signals based on electric charge accumulated in the capacitance elements C1 of the pixels S11 to S13 arranged in the first row are simultaneously output to the signal wires M1 to M3. The electrical signals output to the signal wires M1 to M3 are read by the readout circuit 108. The electrical signals read by the readout circuit 108 are amplified by the operational amplifiers A1 to A3. When the electrical signals are read out, the reset switches Sw1 to Sw4 connected to the operational amplifiers A1 to A3, respectively, are open.

Subsequently, the switches Sr1 to Sr3 of the sample and hold circuit are switched to a conductive state so that the electrical signals amplified by the operational amplifiers A1 to A3 are accumulated in the capacitors CL1 to CL3 of the sample and hold circuit, respectively. After the electrical signals are accumulated in the capacitors CL1 to CL3, the switches Sr1 to Sr3 are switched to a non-conductive state. Thus, the capacitors CL1 to CL3 are electrically disconnected from the signal wires M1 to M3. Thereafter, the operational amplifiers A1 to A3 and the signal wires M1 to M3 are reset using the reset switches Sw1 to Sw4 so as to be ready for processing the output of electrical signals from the next row. The above-described series of operations is referred to as a "readout operation".

The electrical signals sampled and held in the capacitors CL1 to CL3 are sequentially output by the multiplexer Sr4 so that the parallel signals are converted into a serial signal. These electrical signals are sequentially read by the amplifier B. In this way, the electrical signals accumulated in the capacitors CL1, CL2, and CL3 can be sequentially output in this order. At that time, an amount of the electric charge accumulated in a capacitor Cf4 of the amplifier B varies every time the electrical signal is output. Accordingly, every time the multiplexer Sr4 selects one of the capacitors CL1 to CL3, a switch Sw4 needs to be short-circuited so that the capacitor Cf4 is returned to an initial state. Thus, the multiplexer Sr4 sequentially outputs electrical signals based on the electric charge of the pixels S11 to S13 arranged in the first row to the amplifier B as analog electrical signals. The amplifier B performs impedance transformation on these analog electrical signals. The A/D converter 121 then converts the analog signals into digital signals. Thereafter, the digital signals are output as a digital image signal. Hereinafter, such a series of operations is referred to as an "output operation".

Similarly, the readout operation and the output operation are sequentially performed for the second row and the third row. In this way, a digital image signal for one row is output from the readout circuit 108. In addition, according to the present embodiment, for example, the output operation for the first row is temporally overlapped with the readout operation for the second row in the same period of time. Accordingly, the time required for a photographing operation for acquiring an image signal for one image can be reduced as compared with the case where the readout operation for the second row is performed after the output operation for the first row is completed.

A method for controlling the radiation imaging apparatus and the radiation imaging system according to the present embodiment is described next.

The characteristics of the radiation imaging apparatus and the radiation imaging system and the acquired image signal vary in accordance with an elapsed time from the moment that the apparatus is powered on until a bias is applied to the conversion elements, a period of time during which a photographing operation is performed, and an amount of radiation or light exposure of the radiation imaging apparatus. To address this issue, according to the present invention, the radiation imaging apparatus and the radiation imaging system emit a light ray having no image information that is different from a radiation ray or a light ray having image information emitted from the light source 105 to the sensor panel 102. In this way, variations in the characteristics of the apparatus and the image signal are reduced. However, if a light ray having no image information is emitted every time the photographing operation is performed, the performance of the conversion elements and the light source 105 for emitting light is deteriorated. Therefore, it is desirable that, after the required amount of light is emitted, the emission of light from the light source 105 is stopped.

However, the present inventor has discovered that as time elapses after the emission of light is stopped, the effect of reducing the above-described variations decreases. Here, an example result of an experiment examining variation in the sensitivity of the radiation imaging apparatus (variation in the output of the apparatus when a photographing operation for light having a constant intensity is continuously performed) is described with reference to FIGS. 14A to 14C. As used herein, the term "sensitivity" refers to an input/output characteristic of the conversion element obtained on the basis of the output acquired when the conversion element is irradiated with a radiation ray or a light ray having a constant intensity. In this experiment, a bias was applied to the conversion element, and a light ray having no image information was emitted to the conversion element. Thereafter, a radiation ray or a light ray having a constant intensity was repeatedly emitted to the conversion element, and a photographing operation was performed. At that time, a change in the output was measured as a change in the sensitivity.

FIG. 14A is a timing diagram of the radiation imaging system used in the experiment. In FIG. 14A, the abscissa represents a time. The ordinate represents, from the top down, a light emitting operation of a light ray having no image information, a photographing operation of a radiation ray or a light ray having a constant intensity, the sensitivity, and the dark output value. As used herein, the term "dark output value" refers to an output from an imaging apparatus obtained in a dark state in which no radiation ray or light ray is input to the imaging apparatus. The dark output value includes an amount of fixed pattern noise of the imaging apparatus. This dark output value was obtained through the above-described operation sequence, however, in which a radiation ray is not emitted in the accumulating operation when the photographing operation is performed.

Figure 14B:
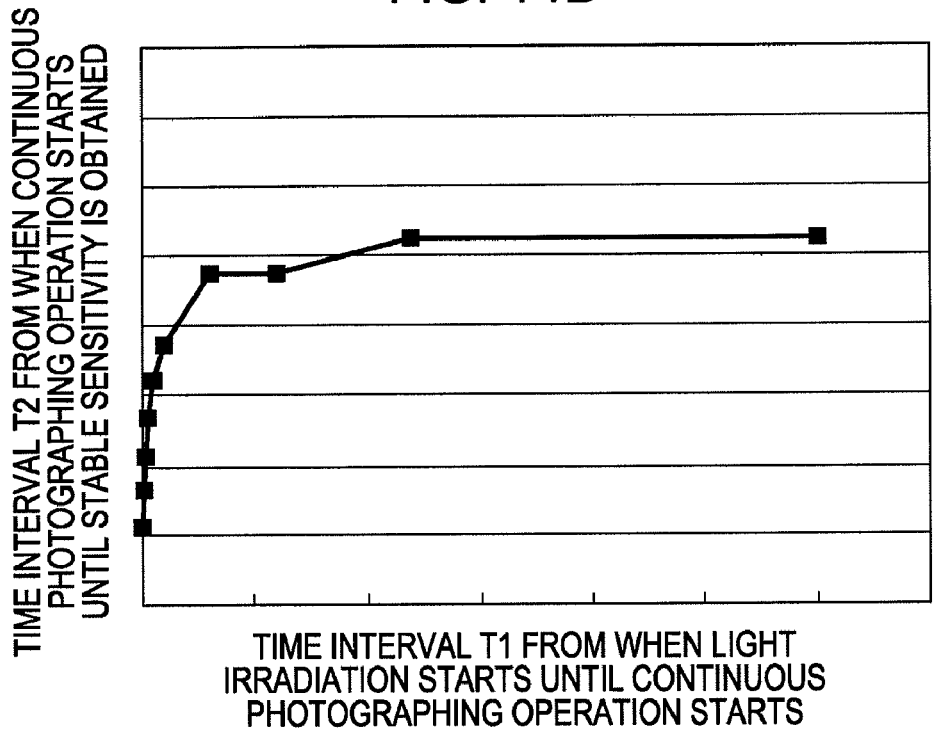
FIG. 14B is a graph illustrating a change in a time T2 from the moment that a readout operation of a first image signal starts until stable sensitivity is obtained in accordance with a change in a time T1 from the moment that the light ray having no image information is emitted until a photographing operation for a first image signal is started.

FIG. 14B is a graph illustrating a change in a time T2 from the moment that a readout operation of a first image signal starts until the stable sensitivity is obtained in accordance with a change in a time T1 from the moment that the light ray having no image information is emitted until a photographing operation for a first image signal is started. In FIG. 14B, the abscissa represents a time. The ordinate represents the time T2 from the moment that a readout operation of a first image signal starts until a stable sensitivity is obtained. As can be seen from FIG. 14B, as the time T1 from the moment that the light ray having no image information is emitted until a photographing operation for a first image signal is started increases, the time T2 until a stable sensitivity is obtained increases. That is, as time elapses, the effect of reducing the change obtained by emitting the light ray having no image information decreases. Accordingly, when continuous photographing operations are performed without a light ray having no image information being emitted, variation in the output may occur, and therefore, the operability may deteriorate. In addition, as the time T1 increases, the dark current more frequently varies. Thus, like the time T2 until a stable sensitivity is obtained, the dark output value varies due to the variation in the dark current.

Figure 14C:
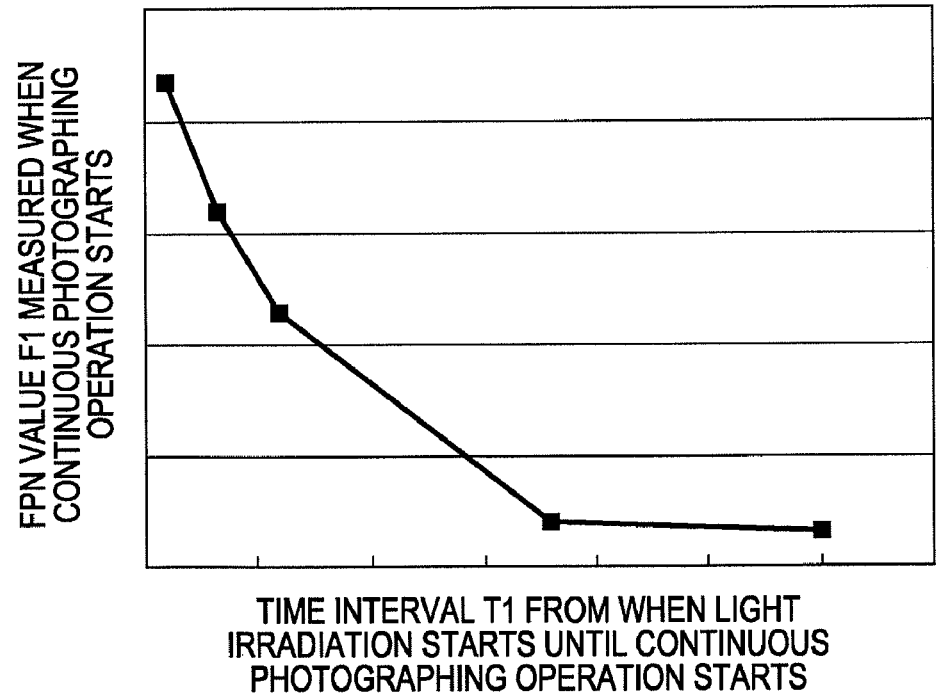
FIG. 14C is a graph illustrating a change in the dark output value in accordance with a change in a time T1 from the moment that the light ray having no image information is emitted until a photographing operation for a first image signal is started.

FIG. 14C is a graph illustrating a change in the dark output value in accordance with a change in a time T1 from the moment that the light ray having no image information is emitted until a photographing operation for a first image signal is started. As can be seen from FIG. 14C, as the time T1 increases, the dark output value decreases. That is, as can be seen from FIGS. 14B and 14C, there is a correlation between a change in the sensitivity and a change in the dark output value. FIGS. 14B and 14C indicate that as the time T1 decreases, the time T2 until the stable sensitivity is obtained decreases, and therefore, the effect of reducing the change increases. However, the dark output value increases. In contrast, as the time T1 increases, the time T2 until the stable sensitivity is obtained increases, and therefore, the effect of reducing the change decreases. However, the dark output value decreases. That is, there is a correlation between the time T2 until the stable sensitivity is obtained and the change in the dark output value. By observing a change in the dark output value, the stabilization level of a change in the sensitivity can be detected. Accordingly, it can be determined that the required effect of reducing the change cannot be obtained when the dark output value reaches a predetermined value.

By determining the predetermined value to be a reference value and comparing the reference value with the dark output value, it can be determined that the required effect of reducing the change cannot be obtained. If the instability of the sensitivity is a problem when the image quality is evaluated, a photographing operation can be performed immediately after the light is emitted. At that point of time, variation in the sensitivity is stabilized in a short time, and therefore, the photographing operation can be performed in a stable condition, although the dark output value is large. However, depending on the type or structure of the conversion element, when light is emitted, the dark output value may increase. Even in such a case, it is desirable that a photographing operation is performed immediately after the light is emitted. At that time, the dark output value increases and the stable sensitivity is obtained in a short time.

Note that the above-described result of an experiment is only an example. In addition to the above-described sensitivity and change in the dark current, the occurrence of image ghosting, for example, varies as time elapses after a light ray having no image information is emitted. As described above, through the experiment, the present inventor has discovered that as time elapses after the emission of a light ray having no image information is stopped, the effect of reducing the variations decreases. In addition the inventor discovered that there is a correlation between a time interval required until variation in the sensitivity is stabilized or the effect of reducing the variation due to the time interval and a change in the dark output value.

In the present embodiment, a dark output value is focused on. The control unit 107 performs control using a dark output value or dark output image information based on dark output values for one image acquired in advance. Note that, according to the present invention, a dark output value or a dark output image based on the dark output values for one image is used as a dark output signal. When a light ray having no image information is emitted from the light source 105 to the conversion elements D1 to D9 after a bias is applied to the conversion elements D1 to D9, an effect of reducing variation in the sensitivity of the output of the sensor panel 102 can be obtained. However, as time elapses after the emission of the light ray having no image information, the effect of reducing the variation in sensitivity decreases. A photographer or an observer of the captured image may feel dissatisfied due to the decrease in the effect of reducing the variation in sensitivity. Accordingly, the reduction in the effect of reducing the variation in sensitivity needs to be a level that is acceptable to the observer. In addition, the decrease in the effect of reducing the variation in sensitivity increases the occurrence of image ghosting. This increase may also make the observer of the image feel dissatisfied.

It is difficult to clearly determine how much of a decrease in the effect of reducing the variation in sensitivity makes the observer of the image feel dissatisfied or what percent of the variation in sensitivity makes the observer of the image feel dissatisfied, since the determination depends on subjective evaluation. However, some criterion for an allowable value needs to be defined. According to the present embodiment, control is performed using the dark output value or the dark output image (a dark output signal) obtained when an observer feels dissatisfied with an image as a reference value. This reference value is determined by the observer or image processing software evaluating the quality of an image acquired in advance.

Figure 3:
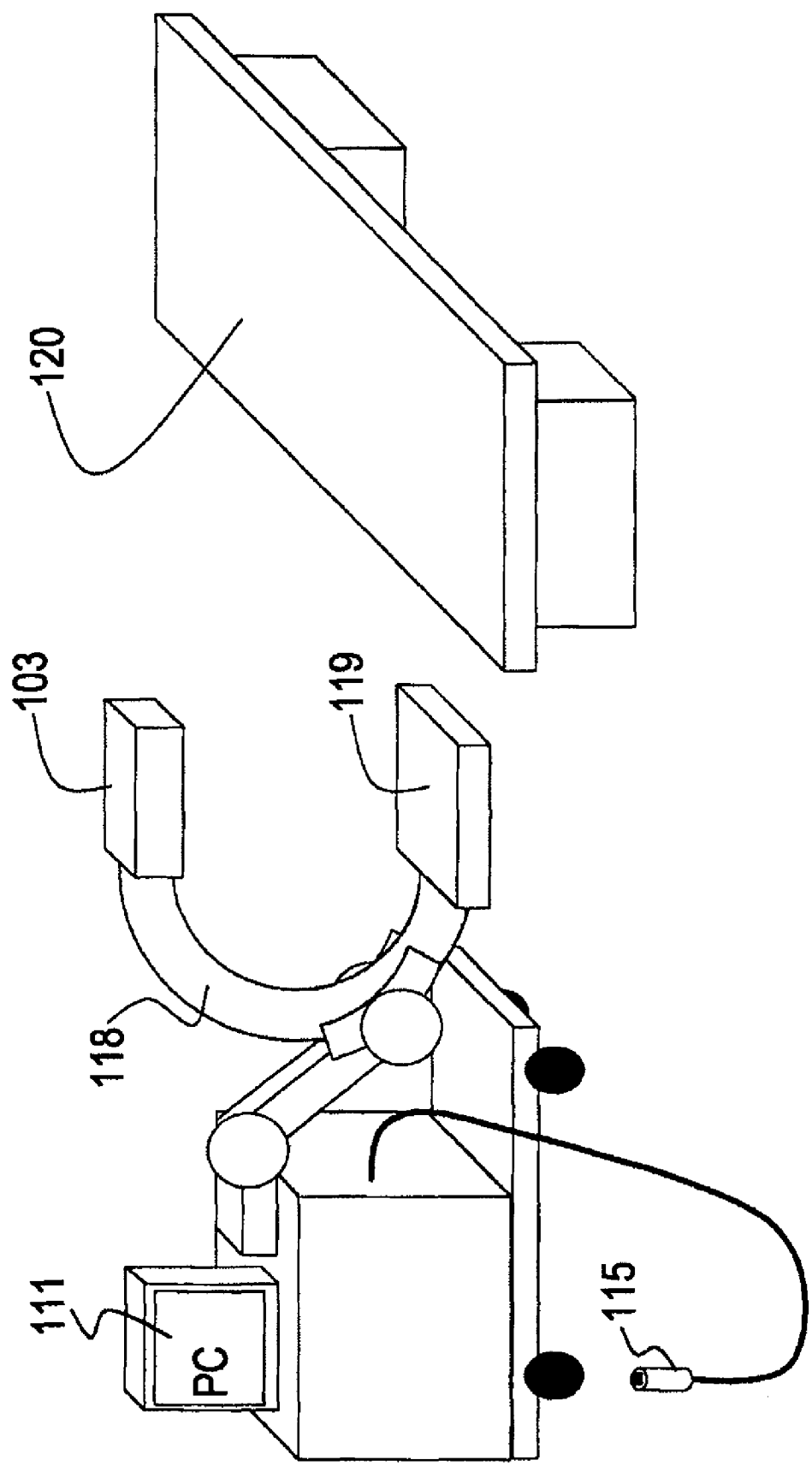
FIG. 3 is a schematic illustration of the radiation imaging apparatus and the radiation imaging system according to the first embodiment of the present invention.
Figure 4:
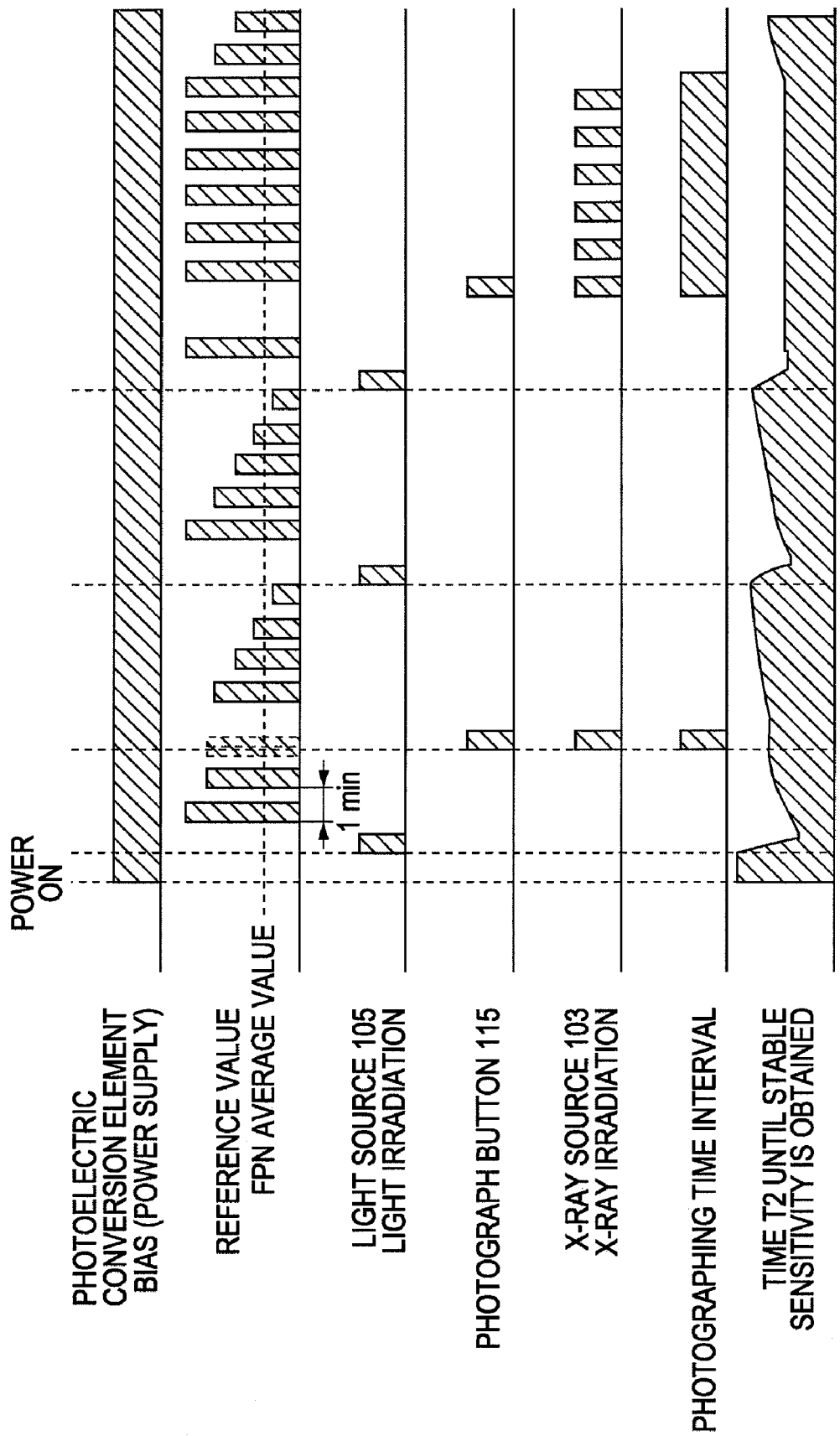
FIG. 4 is a timing diagram of the operations performed by the radiation imaging apparatus and the radiation imaging system during a photographing operation of a subject according to the first embodiment of the present invention.

A radiation imaging apparatus and a radiation imaging system according to the present embodiment that address the above-described issue and exemplary operations thereof are described next. FIG. 3 is a schematic illustration of the radiation imaging apparatus and the radiation imaging system according to the present embodiment of the present invention. FIG. 4 is a timing diagram of when the radiation imaging apparatus and the radiation imaging system capture the image of a subject.

As illustrated in FIG. 3, a C arm 118 takes X-rays for medical fluoroscopy. The C arm 118 includes a flat panel detector 119 and the radiation source 103. Like the flat panel detector illustrated in FIG. 1, a housing (not shown) of the flat panel detector 119 includes the wavelength converter 104, the sensor panel 102, the drive circuit 110, the readout circuit 108, and the light source 105. The radiation source 103 is mounted on the C arm 118 so as to face the flat panel detector 119. While the present embodiment is described with reference to the flat panel detector 119 mounted on the C arm 118, the present invention is not limited thereto. For example, the flat panel detector 119 may be disposed at a fixed location, such as on an upright stand. Alternatively, the flat panel detector 119 may be portable in the form of a cassette.

The flat panel detector 119 supported by the C arm 118 is connected to a personal computer (PC) 111 via a cable or wireless communication. The operation of the flat panel detector 119 is synchronized with the operation of the radiation source 103 via the PC 111. The PC 111 includes the control unit 107 illustrated in FIG. 1. A photographer (such as an engineer or a doctor) can view the captured image through a display of the PC 111. The PC 111 further includes the image processing circuit 122 illustrated in FIG. 1. The PC 111 acquires the output of the sensor panel 102 via the readout circuit 108 as a digital image signal, and performs image processing on the digital image signal. According to the present embodiment, the PC 111 controls a light emitting operation performed by the light source 105 on the basis of the operational state of the radiation source 103 and information obtained by computing the acquired dark output value and a dark output image composed of the dark output values for one image. The conditions for emitting light from the light source 105 are described in detail below.

An example of a drive operation and photographing timing are described next.

The radiation imaging apparatus is powered on first. A bias is applied to the conversion elements D1 to D9 of the sensor panel 102. Subsequently, the conversion elements D1 to D9 are irradiated with a light ray having no image information and emitted from the light source 105. Thereafter, in the above-described photographing operation, the accumulating operation is performed without emitting a radiation ray. In other operations, the dark output value is periodically acquired through the same operation sequence. According to the present embodiment, the dark output value is acquired every one minute. At that time, the radiation ray emitted from the radiation source 103 and a light ray having no image information and emitted from the light source 105 are not emitted to the sensor panel 102. The acquired dark output values and a dark output image (a dark output signal) based on the acquired dark output values are output to the PC 111 including the control unit 107. Thereafter, the acquired dark output values and the dark output image are processed, and the average value is computed. The control unit 107 compares the obtained dark output value or the dark output image with a pre-acquired and predetermined reference value.

If the average value of the obtained dark output values or the dark output images is less than the pre-acquired reference value, the control unit 107 of the PC 111 activates the light source 105 to emit a light ray having no image information. The conversion elements D1 to D9 are irradiated with the emitted light ray, and therefore, the trap level in each of the conversion elements becomes shallow. Consequently, the dark current, the occurrence of image ghosting, and variation in the sensitivity are reduced, and therefore, a measurement under stable characteristics can be made available. As time elapses, the electric charge in the trap level returns to the state maintained before the light ray is emitted due to, for example, the excitation caused by heat. Therefore, the dark output value or the dark output image is acquired at all times and is compared with the reference value. In this way, it is determined whether emission of a light ray from the light source 105 and irradiation of the light onto the conversion elements are necessary. However, if the timing for acquiring the dark output image overlaps with the timing for acquiring a radiation image, acquisition of the radiation image has first priority. In this way, the throughput of acquiring the radiation image is not degraded.

When the photographer pushes a photograph button 115, the radiation source 103 is made to emit a radiation ray. The radiation imaging apparatus performs a photographing operation. Thus, an image of the subject is generated.

According to the present embodiment, when the reference value of the dark output value or the dark output image is acquired or a bias is applied to the conversion elements during a photographing operation, the dark output value or the dark output image is acquired every one minute. However, in the case where the reference value of the dark output value or the dark output image is obtained, if it can be determined how many frames exist before the photographer feels dissatisfied with the dark output value or the dark output image obtained from a frame, the dark output value or the dark output image may be acquired at an interval greater than or less than one minute. If the interval for acquiring the dark output value or the dark output image is too long, the photographer may feel dissatisfied when the dark output value or the dark output image is obtained from a first frame. In contrast, if the interval for acquiring the dark output value or the dark output image is too short, an enormous number of the dark output values or the dark output images must be examined in order to find the dark output value or the dark output image with which the photographer feels dissatisfied. In the first setting, the issue may not be solved. In the second setting, the operation becomes less efficient. Accordingly, these two settings need to be avoided.

In addition, according to the present embodiment, light irradiation is carried out when the dark output value or the dark output image is less than the reference value. However, depending on the type of sensor, if the effect of the irradiation from the light source 105 is decreased, the dark output value or the dark output image increases. Accordingly, the photographer may feel dissatisfied with an image. In such a case, light irradiation can be carried out when the dark output value or the dark output image is greater than the reference value. Furthermore, according to the present embodiment, the average value of the dark output values or the dark output images is employed. However, one of the dark output values or the dark output images of the sensor panel 102 can be employed. Alternatively, a maximum value or a minimum value of the dark output values or the dark output images may be employed.

According to the present embodiment, only the average value of the dark output values or the dark output images is employed. However, the dark output values or the dark output images vary in accordance with temperature. Therefore, the control unit 107 may include a temperature sensor, and the control unit 107 may change the dark output value or the dark output image serving as a reference value for light irradiation in accordance with the temperature detected by the temperature sensor. In addition, the radiation imaging apparatus need not include the light source 105. Instead of emitting a light ray having no image information from the light source 105, the radiation imaging apparatus may emit a radiation ray having no image information from the radiation source 103.

As noted above, an image having an improved quality can be captured at substantially the same time as the photographer intends to capture the image. More specifically, the dark current, image ghosting, and sensitivity of the imaging apparatus can be stabilized. In addition, the time interval for emitting light to the conversion element can be reduced, and therefore, the power consumption and the heat generation of the light source can be reduced. Furthermore, the durability of the conversion element can be improved.

Second Embodiment

Figure 5:
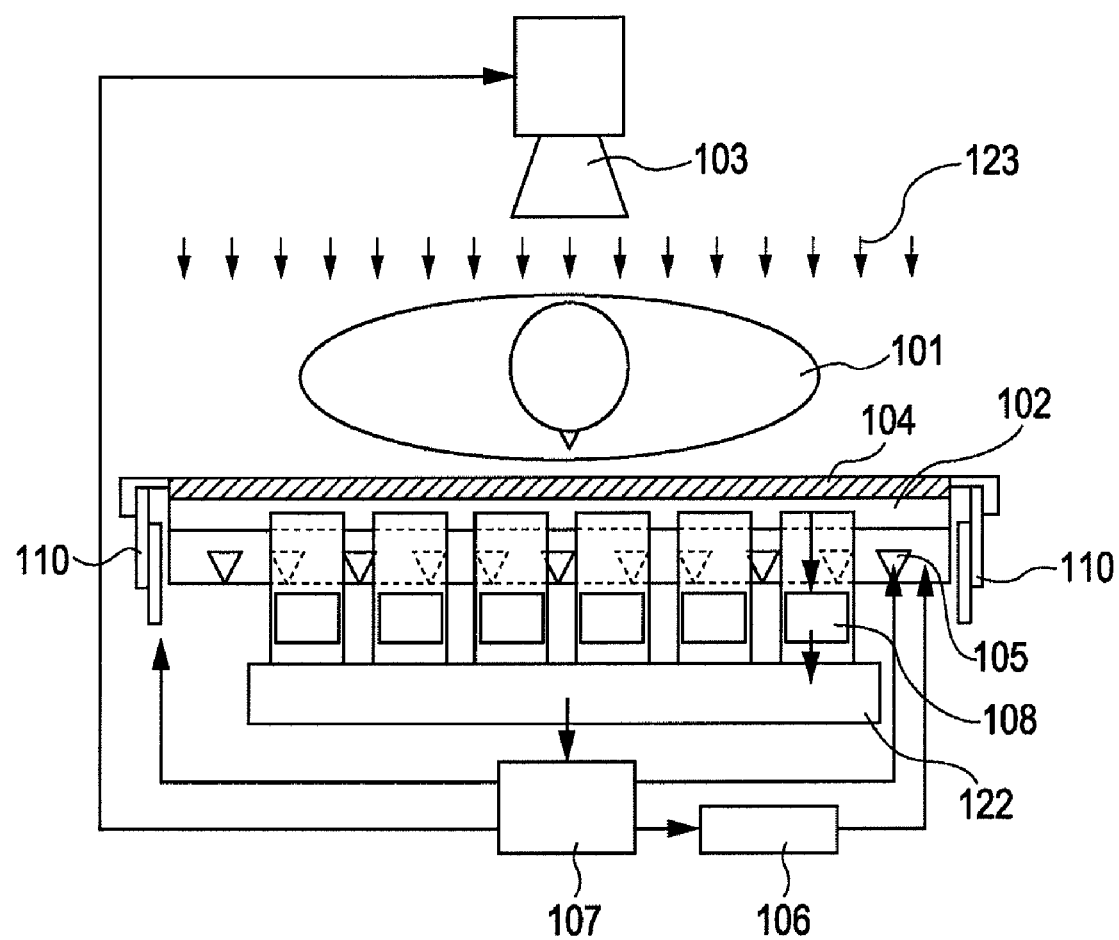
FIG. 5 is a schematic illustration of an exemplary configuration of a radiation imaging system according to a second embodiment of the present invention.

A second embodiment of the present invention is described next with reference to FIG. 5. FIG. 5 is a schematic illustration of an exemplary structure of a radiation imaging system according to the second embodiment of the present invention. Unlike the first embodiment, the radiation imaging system according to the second embodiment includes a timer 106. According to the present embodiment, a dark output value or a dark output image from the image processing circuit 122 is not directly used for control. Like the first embodiment, it is determined whether a photographer feels dissatisfied with an image using a dark output value or a dark output image from the radiation imaging apparatus. An interval between the time when a light ray having no image information is emitted and the time when the determination is made is defined as a reference value. This reference value is stored in the timer 106. Subsequently, the timer 106 outputs time information to the control unit 107 during a photographing operation of a radiation image. The control unit 107 determines whether emission of a light ray from the light source 105 and irradiation of the light onto the conversion elements are necessary on the basis of the time information. In this way, the control unit 107 controls the emission of a light ray having no image information from the light source 105.

More specifically, during a photographing operation of a radiation image, the timer 106 measures the time elapsed from when irradiation of a light ray having no image information from the light source 105 is started. The timer 106 supplies a signal representing the time information to the control unit 107 when the measured elapsed time reaches the reference value, which is the prestored elapsed time until a photographer felt dissatisfied with an image. The control unit 107 instructs the light source 105 to emit a light ray having no image information on the basis of the signal. Thus, the conversion elements are irradiated with the light ray. Since other configurations are similar to those of the first embodiment, detailed descriptions thereof are not repeated.

Figure 6:
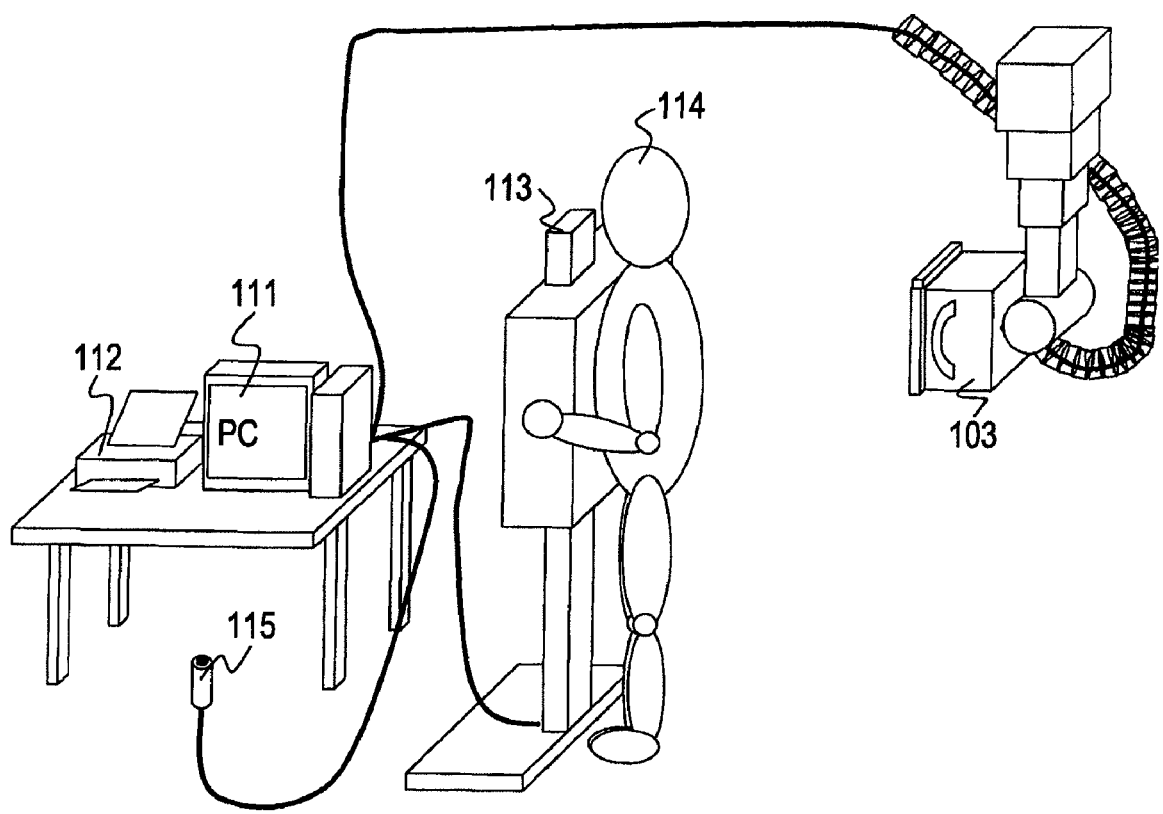
FIG. 6 is a schematic illustration of exemplary structures of the radiation imaging apparatus and the radiation imaging system according to the second embodiment of the present invention.

The radiation imaging apparatus and the radiation imaging system according to the present embodiment are described next with reference to FIG. 6. FIG. 6 is a schematic illustration of exemplary structures of the radiation imaging apparatus and the radiation imaging system according to the present embodiment. However, the radiation imaging system may have a configuration different from this configuration. Unlike the first embodiment illustrated in FIG. 3, the flat panel detector 119 is supported by an upright stand 113 in place of the C arm 118. In addition, the radiation source 103 is secured to a ceiling. Furthermore, a photographer (such as an engineer or a doctor) can print a captured radiation image using a printer 112 via the PC 111. Since other configurations are similar to those of the first embodiment, detailed descriptions thereof are not repeated.

While the timer 106 according to the present embodiment is disposed in the flat panel detector 119, the present invention is not limited thereto. For example, the timer 106 may be disposed in the PC 111.

According to the present embodiment, after corrected images are examined, the above-described elapsed time obtained when the photographer feels dissatisfied may be recorded. For example, a difference between a captured image and the image immediately preceding the captured image may be examined so that it can be determined whether the captured image is acceptable.

Figure 7:
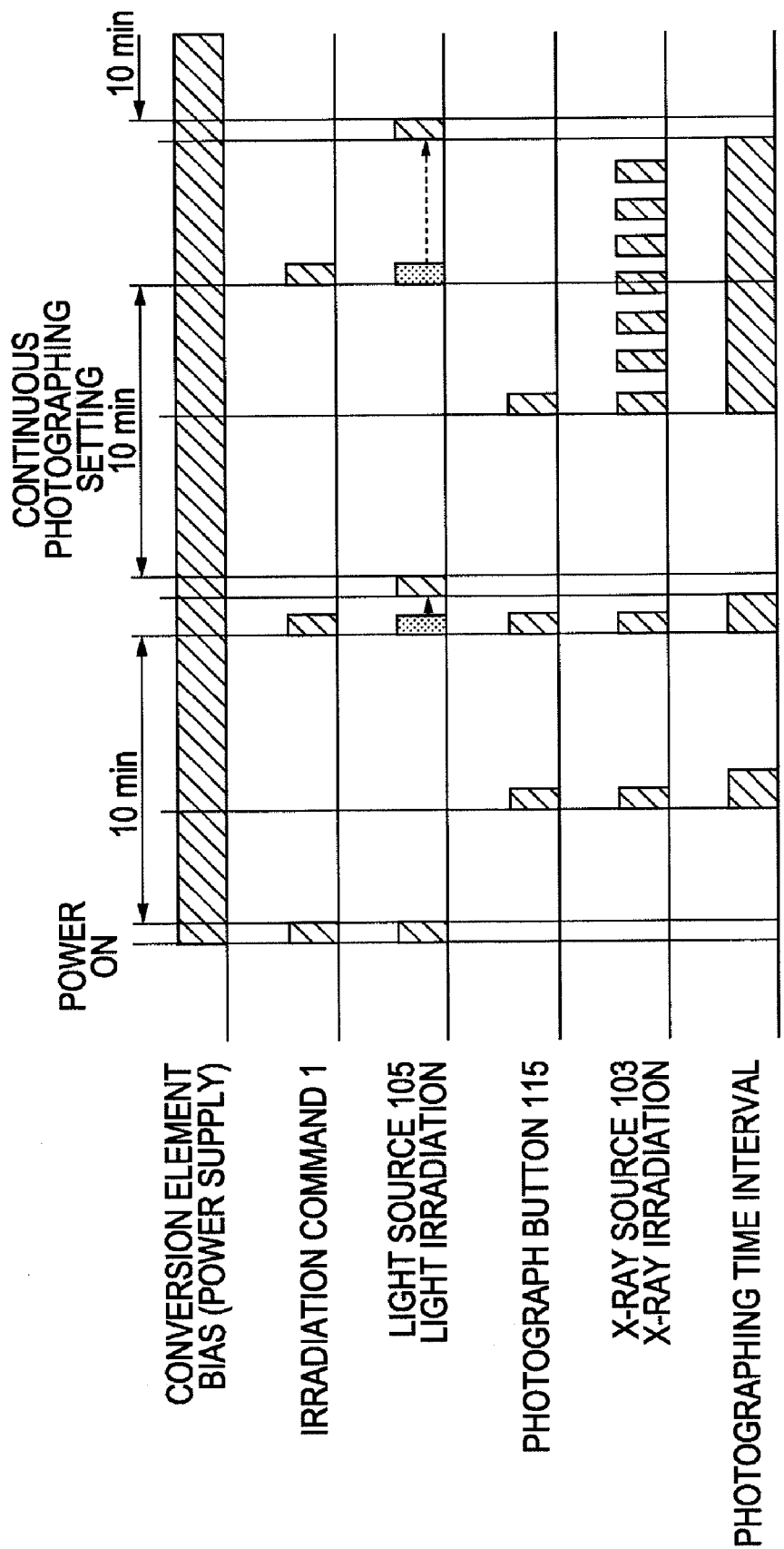
FIG. 7 is a timing diagram of the operations performed by the radiation imaging apparatus and the radiation imaging system during a photographing operation of a subject according to the second embodiment of the present invention.

The operations performed by the radiation imaging apparatus and the radiation imaging system according to the present embodiment are described next with reference to FIG. 7. FIG. 7 is a timing diagram of the operations of the radiation imaging apparatus and the radiation imaging system during a photographing operation of a subject.

The radiation imaging apparatus is powered on first. A bias is applied to the conversion elements D1 to D9 of the sensor panel 102. Subsequently, the timer 106 outputs an irradiation command 1 to the control unit 107 incorporated in the PC 111. The control unit 107 instructs the light source 105 to emit a light ray having no image information. Thus, the conversion elements D1 to D9 of the sensor panel 102 are irradiated with the light ray having no image information and emitted from the light source 105. At that time, the timer 106 starts measuring the time elapsed from when the light ray having no image information is emitted from the light source 105. If the measured time reaches the reference value, which is the prestored elapsed time until a photographer felt dissatisfied with an image, the timer 106 outputs an irradiation command 1 serving as time information to the control unit 107 incorporated in the PC 111. Upon receiving the irradiation command 1, the control unit 107 in the PC 111 instructs the light source 105 to emit a light ray having no image information. Thus, the conversion elements D1 to D9 of the sensor panel 102 are irradiated with the light ray having no image information. If a radiation ray is emitted from the radiation source 103 before the measured time reaches the reference value, the timer 106 starts measuring the time elapsed from when the radiation ray is emitted. Thereafter, the timer 106 compares the time elapsed from when the radiation ray is emitted with the reference value. If the elapsed time is greater than the reference value, the timer 106 outputs an irradiation command 1.

If the timing for outputting the irradiation command 1 overlaps with the timing for acquiring a radiation image, acquisition of the radiation image has first priority. In this way, the throughput of acquiring the radiation image is not degraded. Through the above-described operations, like the first embodiment, the dark current, image ghosting, and sensitivity of the imaging apparatus can be stabilized. In addition, the light emission time to the conversion element can be reduced, and therefore, the power consumption and the heat generation of the light source can be reduced. Furthermore, the durability of the conversion element can be increased. Still furthermore, unlike the first embodiment, the control can be performed without periodically acquiring the dark output value or the dark output image. Consequently, the system load can be reduced.

Third Embodiment

Figure 8A:
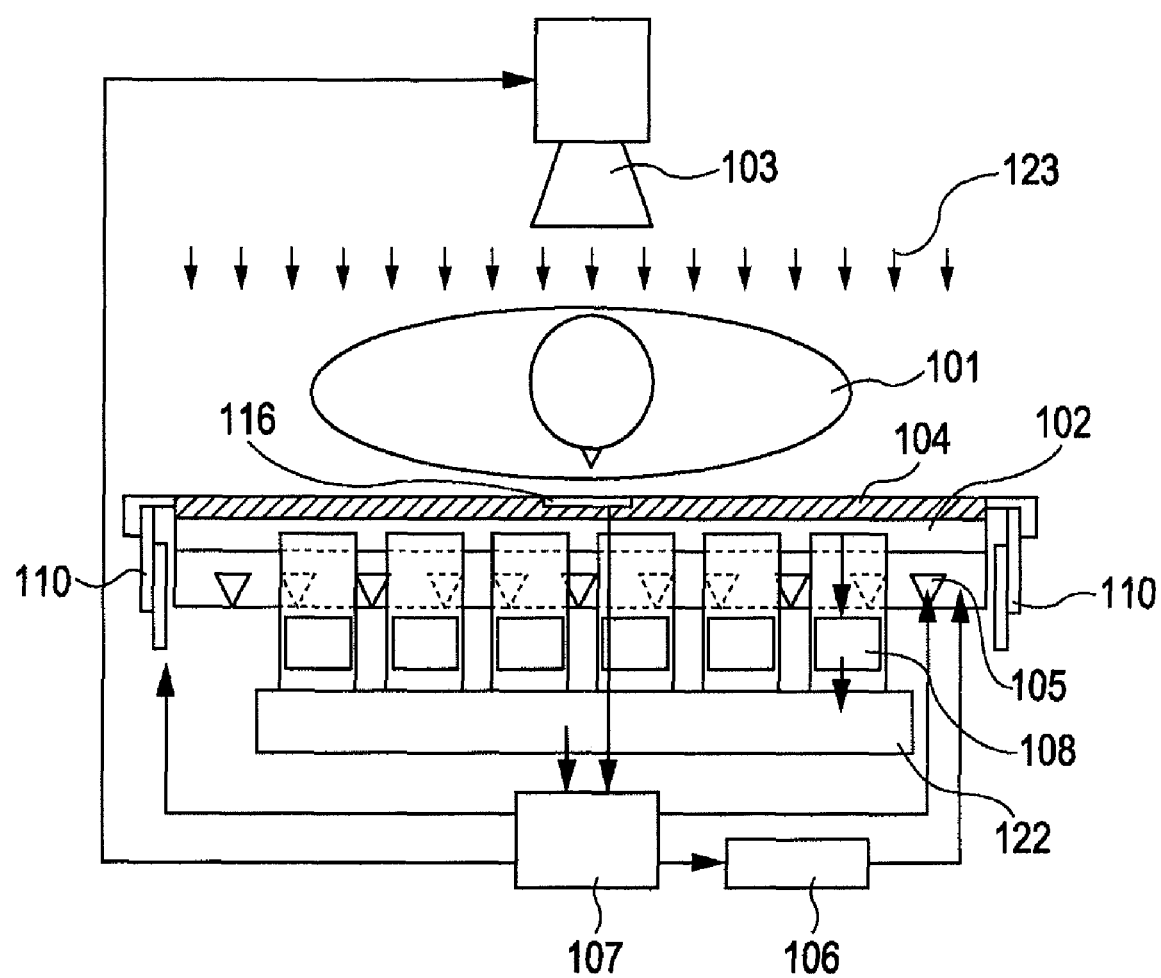
FIGS. 8A and 8B are schematic illustrations of an exemplary configuration of a radiation imaging system according to a third embodiment of the present invention.
Figure 8B:
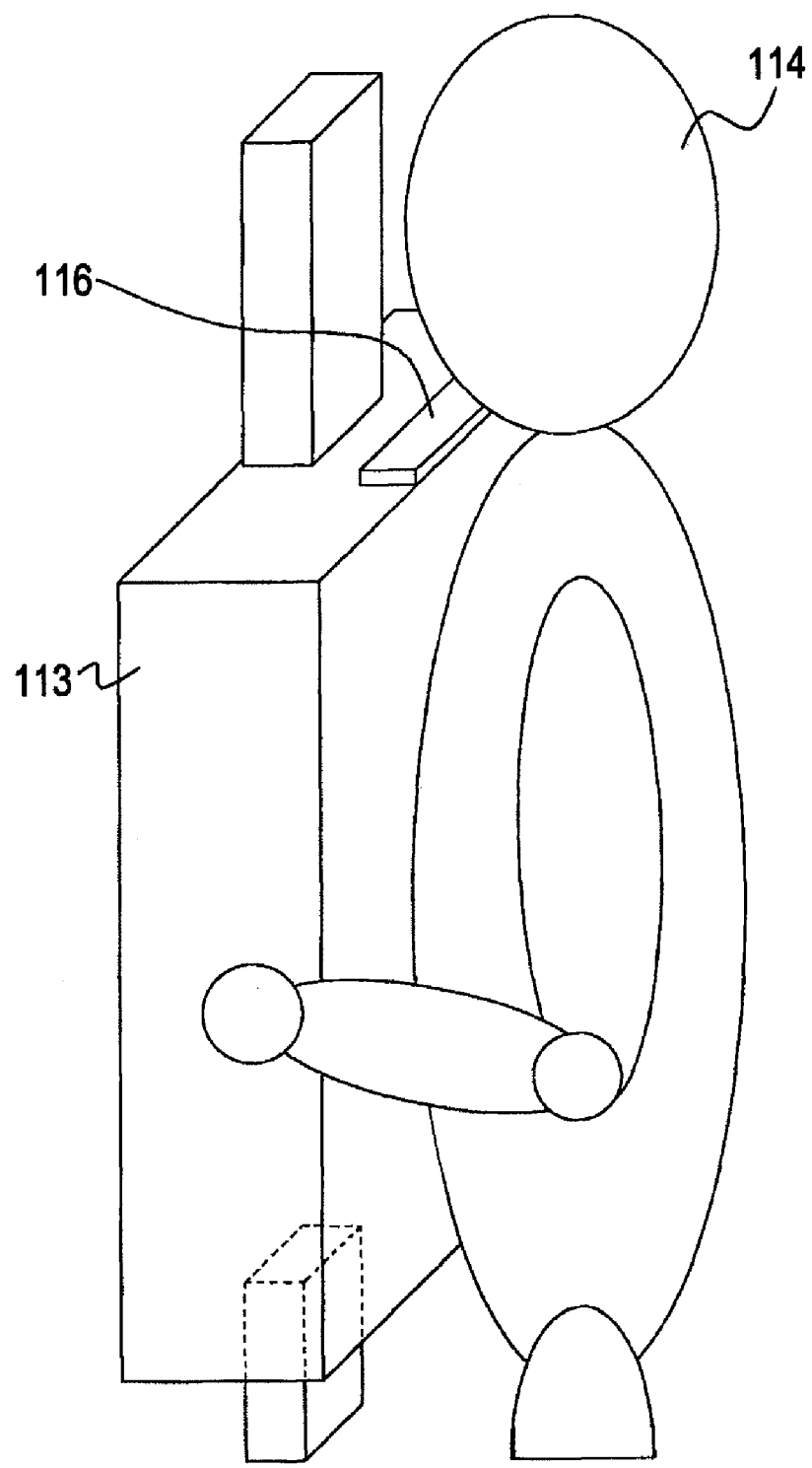

A third embodiment of the present invention is described next with reference to FIGS. 8A and 8B. FIGS. 8A and 8B are schematic illustrations of an exemplary configuration of a radiation imaging system according to the third embodiment of the present invention. The radiation imaging system according to the third embodiment has a configuration similar to that of the second embodiment. In addition, the radiation imaging system according to the third embodiment includes a subject detection sensor 116. The subject detection sensor 116 serves as a unit for detecting information indicating the necessity of light irradiation. The subject detection sensor 116 is controlled by the control unit 107 so as to inform the control unit 107 of the presence of human touch and human proximity. More specifically, a pressure sensor that can detect pressure, a sensor that can detect variation in an electrical current due to contact with a human body, or a temperature sensor that can detect body temperature can be used for the subject detection sensor 116. The subject detection sensor 116 is mounted on the upright stand 113 at a position at which a subject puts their chin during a photographing operation. When a subject 114 puts their chin on the subject detection sensor 116 mounted on the upright stand 113 before a photographing operation starts, the subject detection sensor 116 detects the pressure and outputs a subject detection signal to the control unit 107 incorporated in the PC 111. According to the present embodiment, the control unit 107 incorporated in the PC 111 controls whether a light ray having no image information is emitted from the light source 105 on the basis of the signal output from the timer 106, the subject detection signal output from the subject detection sensor 116, and the state of the radiation source 103. Since other configurations are similar to those of the second embodiment, detailed descriptions thereof are not repeated.

An exemplary method for controlling the radiation imaging system according to the present embodiment is described next with reference to FIG. 9. FIG. 9 is a timing diagram of the operations performed by the radiation imaging apparatus and the radiation imaging system during a photographing operation of a subject.

The radiation imaging apparatus is powered on first. A bias is applied to the conversion elements D1 to D9 of the sensor panel 102. Subsequently, the timer 106 outputs an irradiation command 1 to the control unit 107 incorporated in the PC 111. The control unit 107 instructs the light source 105 to emit a light ray having no image information. Thus, the conversion elements D1 to D9 of the sensor panel 102 are irradiated with the light ray having no image information and emitted from the light source 105. At that time, like the second embodiment, the timer 106 starts measuring the time elapsed from when the light ray having no image information is emitted from the light source 105. If the measured time reaches the reference value, which is the prestored elapsed time until a photographer felt dissatisfied with an image, the timer 106 outputs an irradiation command 1 serving as time information to the control unit 107 incorporated in the PC 111.

In addition, when the subject detection sensor 116 detects that the chin of the subject (a patient) 114 touches the subject detection sensor 116 mounted on the upright stand 113, the subject detection sensor 116 outputs an irradiation command 2 serving as a subject detection signal to the control unit 107 incorporated in the PC 111. Upon receiving the irradiation command 2 after receiving the irradiation command 1, the control unit 107 instructs the light source 105 to emit a light ray having no image information. Thus, the conversion elements are irradiated with the light ray having no image information. If a radiation ray is emitted from the radiation source 103 before the measured time reaches the reference value, the timer 106 starts measuring the time elapsed from when the radiation ray is emitted. Thereafter, the timer 106 compares the time elapsed from when the radiation ray is emitted with the reference value. If the elapsed time is greater than the reference value, the timer 106 outputs an irradiation command 1. Thereafter, until the next irradiation command 1 is received, the light source 105 does not emit a light ray regardless of the input of the irradiation command 2. In a photographing operation, immediately after a photographer pushes the photograph button 115, the apparatus starts a photographing operation. The radiation source 103 is made to emit a radiation ray.

If the timing for outputting the irradiation command 2 from the subject detection sensor 116 overlaps with the timing for acquiring a radiation image, acquisition of the radiation image has first priority. In this way, the throughput of acquiring the radiation image is not degraded. If the irradiation command 1 has been output from the timer 106, light irradiation is performed when the irradiation command 2 is output again after the photographing operation is completed.

Figure 10:
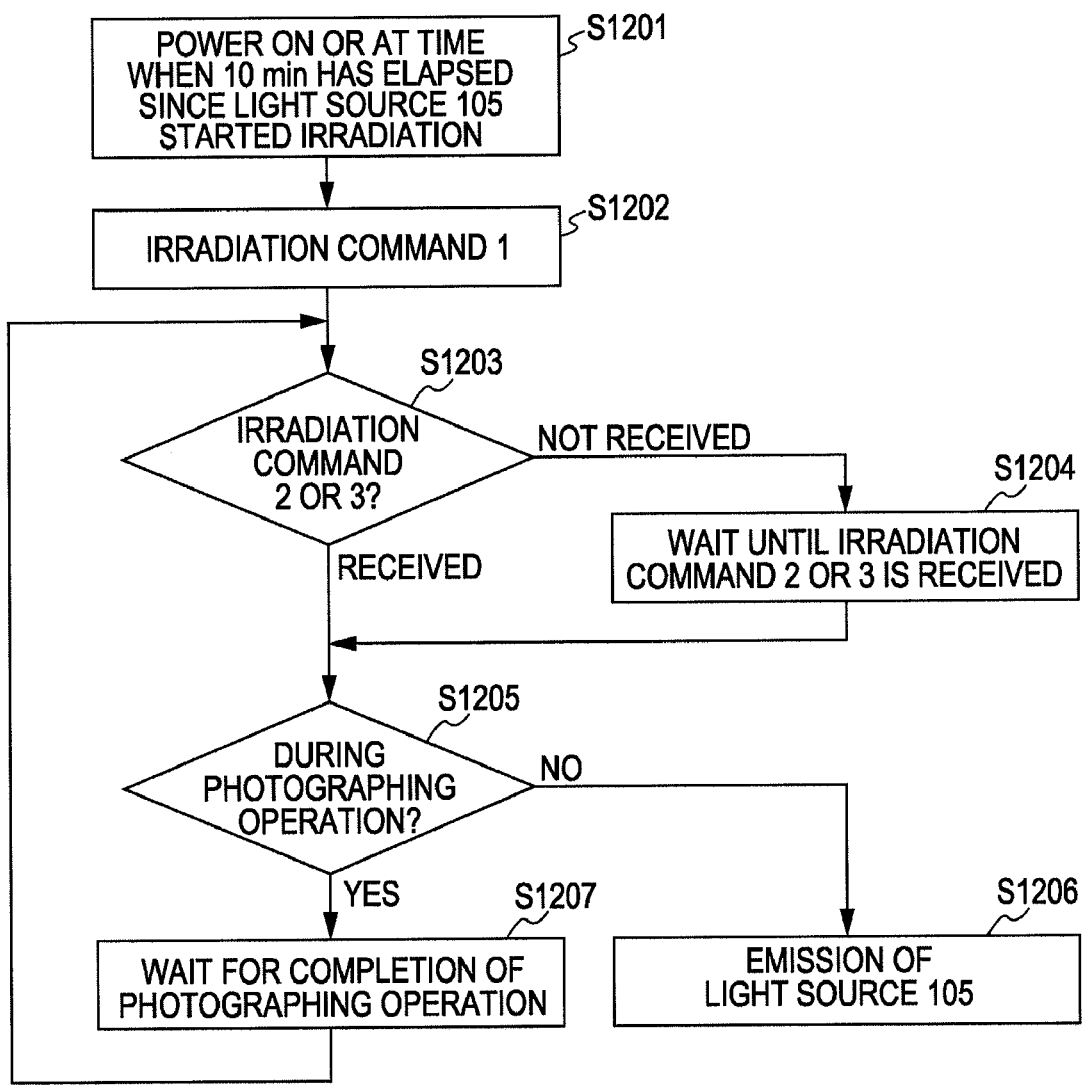
FIG. 10 is a flow chart illustrating a control method according to the third embodiment.

FIG. 10 is a flow chart illustrating the above-described control method according to the present embodiment. In step S1201, if a predetermined time representing the reference time has elapsed since the power was turned on or light irradiation by the light source 105 started, the process proceeds to step S1202. In step S1202, the timer 106 outputs an irradiation command 1 to the control unit 107 incorporated in the PC 111. Subsequently, in step S1203, the control unit 107 incorporated in the PC 111 determines whether it has received the irradiation command 2 from the subject detection sensor 116. If the control unit 107 has received the irradiation command 2, the process proceeds to step S1205. However, if the control unit 107 has not received the irradiation command 2, the process proceeds to step S1204. Note that an irradiation command 3 is described below with reference to a fourth embodiment. In step S1204, the control unit 107 incorporated in the PC 111 causes the flat panel detector to wait for the next input of the irradiation command 2. If the control unit 107 detects the input of the irradiation command 2, the process proceeds to step S1205. In step S1205, the control unit 107 incorporated in the PC 111 determines whether the apparatus is in a photographing operation period. If the apparatus is in a photographing operation period, the process proceeds to step S1207. However, if the apparatus is not in a photographing operation period, the process proceeds to step S1206. In step S1207, the control unit 107 incorporated in the PC 111 waits for completion of the photographing operation period, and the process returns to step S1203. In step S1206, the control unit 107 incorporated in the PC 111 instructs the light source 105 to emit a light ray.

Through the above-described operations, like the first embodiment, the dark current, image ghosting, and sensitivity of the imaging apparatus can be stabilized. In addition, the time period in which light is emitted to the conversion elements can be reduced, and therefore, the power consumption and the heat generation of the light source can be reduced. Furthermore, the durability of the conversion element can be increased. Still furthermore, unlike the first embodiment, control can be performed without periodically acquiring the dark output value or the dark output image. Consequently, the system load can be advantageously reduced. Yet still furthermore, by using the subject detection sensor 116, the number of light irradiation operations performed by the light source 105 can be reduced when the subject is not located at a position at which a photographing operation is available, as compared with the second embodiment.

Fourth Embodiment

Figure 11:
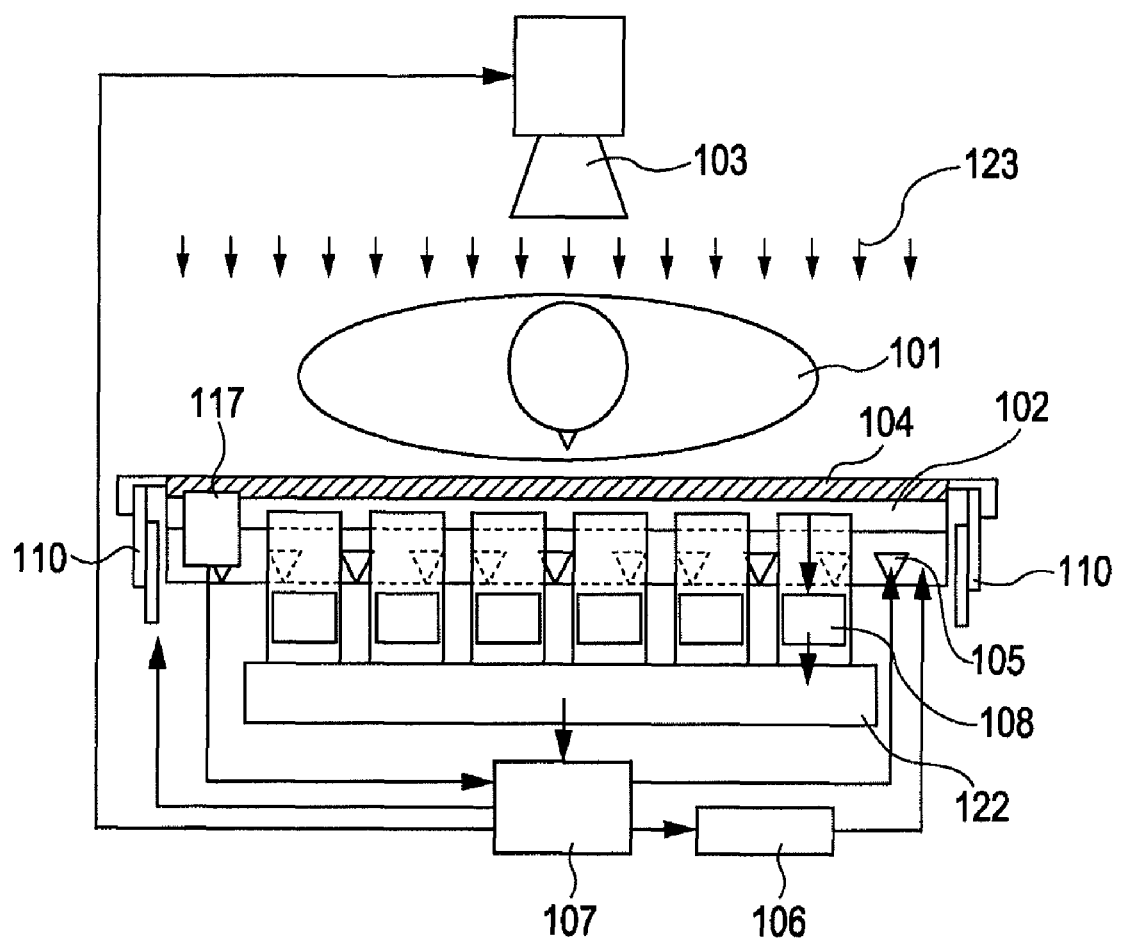
FIG. 11 is a schematic illustration of an exemplary configuration of a radiation imaging system according to a fourth embodiment of the present invention.

A radiation imaging apparatus and a radiation imaging system according to a fourth embodiment is described next with reference to FIG. 11. FIG. 11 is a schematic illustration of an exemplary structure of a radiation imaging system according to the fourth embodiment of the present invention. Unlike the third embodiment, the radiation imaging system according to the fourth embodiment includes a position detection sensor 117 in place of the subject detection sensor 116. The position detection sensor 117 serves as a unit for detecting information indicating the necessity of light irradiation. The position detection sensor 117 is controlled by the control unit 107 so as to inform the control unit 107 of information about the position of the sensor panel 102. More specifically, an infrared ray sensor or a gyro sensor can be used for the position detection sensor 117. However, any sensor that can detect the inclination and direction of the sensor panel 102 can be used for the position detection sensor 117. The positional information transmitted to the control unit 107 may be a binary value that represents whether or not a subject is located at a position at which a photographing operation is available, a digital value that represents information such as an angle or a position, or an analog value that represents information such as an angle or a position. In the case where a digital value or analog value represents information such as an angle or a position, the control unit 107 determines whether or not a subject is located at a position at which a photographing operation is available using a predetermined condition set at the shipping time or by an operator. Since other configurations are similar to those of the third embodiment, detailed descriptions thereof are not repeated.

Figure 12:
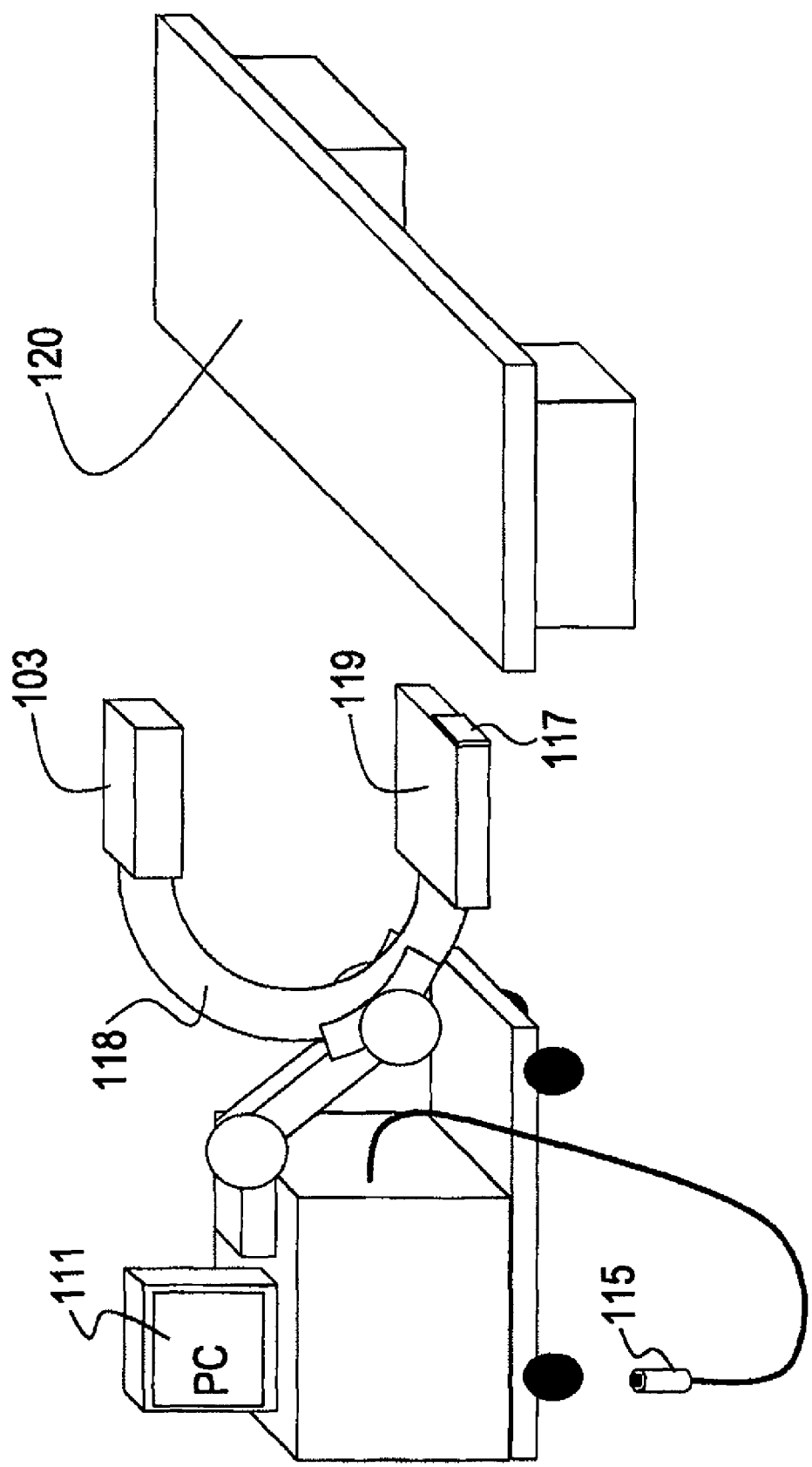
FIG. 12 is a schematic illustration of exemplary structures of a radiation imaging apparatus and the radiation imaging system according to the fourth embodiment of the present invention.

FIG. 12 is a schematic illustration of exemplary configurations of the radiation imaging apparatus and the radiation imaging system according to the present embodiment. That is, FIG. 12 is an external view of the radiation imaging system according to the present embodiment. The radiation imaging system includes a flat panel detector similar to that of the first embodiment of the present invention and illustrated in FIG. 3. However, the flat panel detector further includes the position detection sensor 117. Since other configurations are similar to those of the first embodiment, detailed descriptions thereof are not repeated.

According to the present embodiment, the position detection sensor 117 is composed of an infrared ray sensor. The position detection sensor 117 can detect whether a bed 120 is located in the proximity of the position detection sensor 117. When the position detection sensor 117 disposed in the C arm 118 moves towards the bed 120 and the radiation imaging apparatus enters a state in which the radiation imaging apparatus can perform a photographing operation, the position detection sensor 117 outputs a signal to the PC 111. According to the present embodiment, an infrared ray sensor is used for the position detection sensor 117. However, any sensor that can inform the control unit 107 incorporated in the PC 111 of the positional information can be used for the position detection sensor 117. The control unit 107 incorporated in the PC 111 controls whether a light ray having no image information is emitted from the light source 105 on the basis of the signal output from the timer 106, the position detection signal output from the position detection sensor 117, and the state of the radiation source 103.

Figure 13:
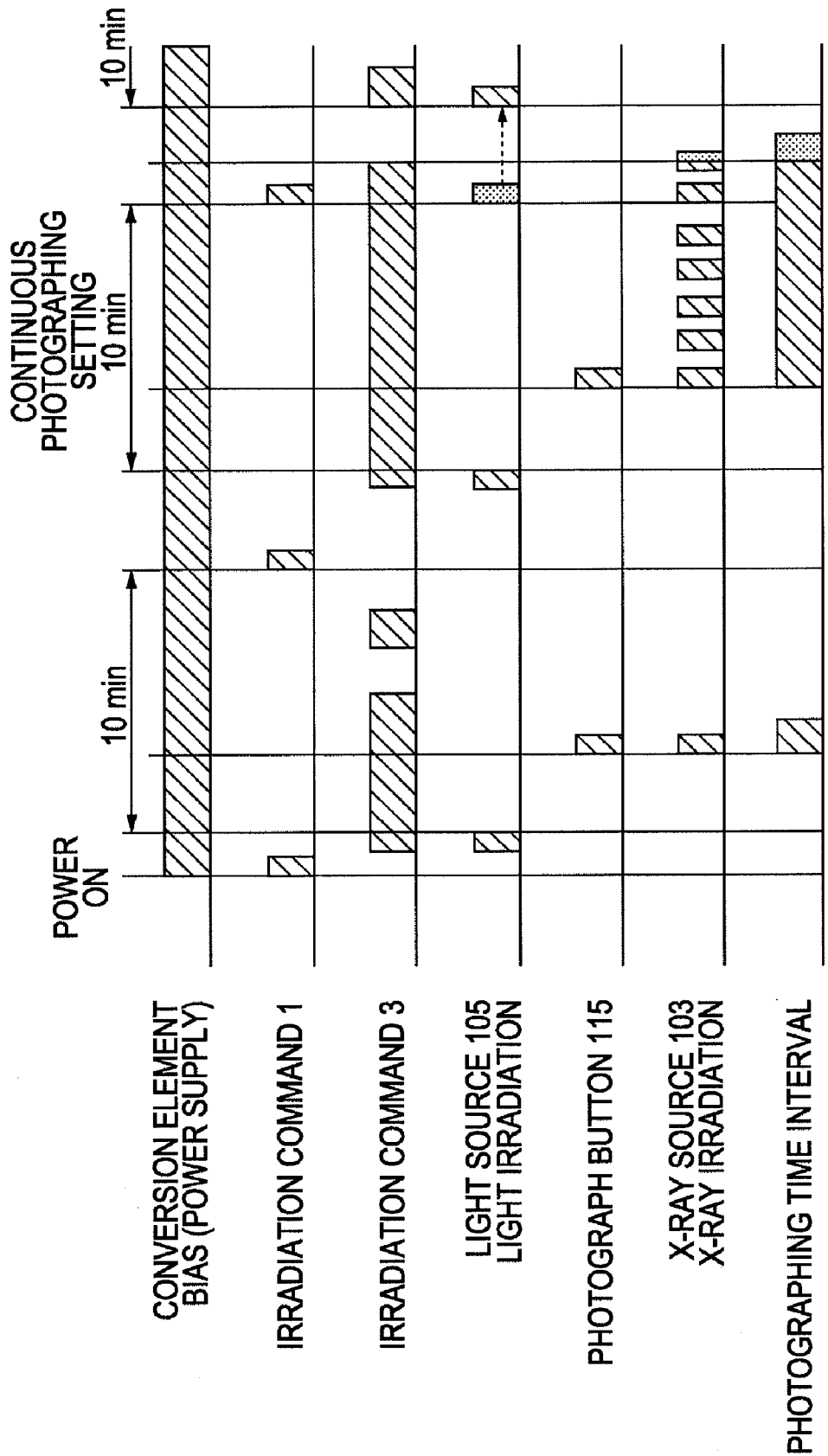
FIG. 13 is a timing diagram of the operations performed by the radiation imaging apparatus and the radiation imaging system during a photographing operation of a subject according to the fourth embodiment of the present invention.

An exemplary method for controlling the radiation imaging system according to the present embodiment is described next with reference to FIG. 13. FIG. 13 is a timing diagram of the operations performed by the radiation imaging apparatus and the radiation imaging system during a photographing operation of a subject. According to the present embodiment, the irradiation command 2 output from the subject detection sensor 116 according to the third embodiment is replaced by an irradiation command 3, which is the position detection signal output from the position detection sensor 117. Since other control is similar to that of the third embodiment, detailed description thereof is not repeated.

Through the above-described operations, like the first embodiment, the dark current, image ghosting, and sensitivity of the imaging apparatus can be stabilized. In addition, the light emission time to the conversion elements can be reduced, and therefore, the power consumption and the heat generation of the light source can be advantageously reduced. Furthermore, the durability of the conversion element can be increased. Still furthermore, unlike the first embodiment, control can be performed without periodically acquiring the dark output value or the dark output image. Consequently, the system load can be advantageously reduced. Yet still furthermore, like the third embodiment, by using the position detection sensor 117, the number of light irradiation operations performed by the light source 105 can be reduced when the subject is not located at a position at which a photographing operation is available, as compared with the second embodiment.

Figure 15:
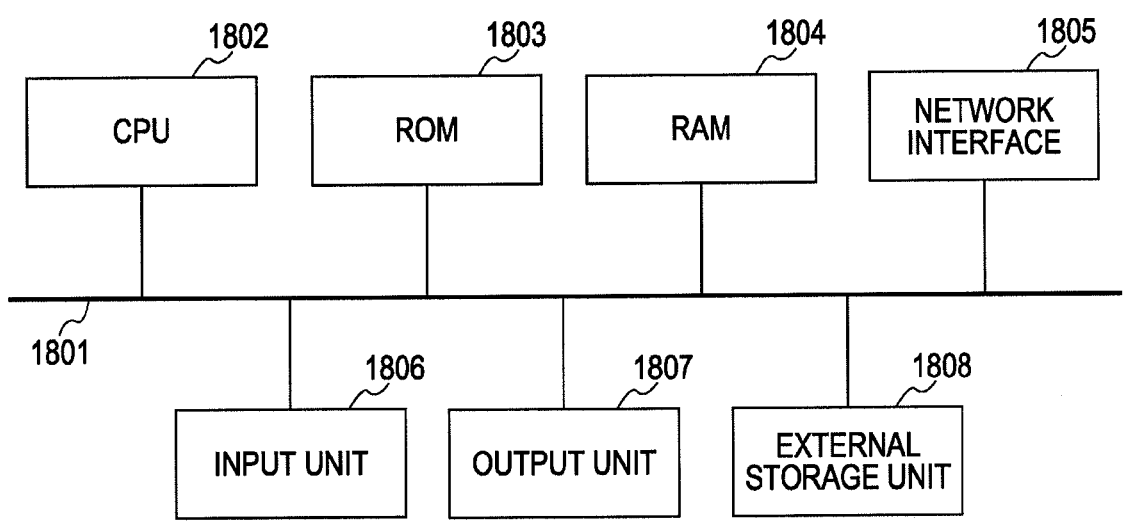
FIG. 15 is a block diagram of an exemplary hardware configuration of a personal computer according to the first to fourth embodiments.

FIG. 15 is a block diagram of an exemplary hardware configuration of the PC 111 according to the first to fourth embodiments. The following devices are connected to a bus 1801: a central processing unit (CPU) 1802, a read only memory (ROM) 1803, a random access memory (RAM) 1804, a network interface 1805, an input unit 1806, an output unit 1807, and an external storage unit 1808.

The CPU 1802 processes or computes data. In addition, the CPU 1802 controls various devices connected to the CPU 1802 via the bus 1801. The CPU 1802 corresponds to the control unit 107. The ROM 1803 prestores the control sequence (a computer program) performed by the CPU 1802. When the CPU 1802 executes the computer program, the control sequence is started. A computer program is stored in the external storage unit 1808. After the computer program is loaded into the RAM 1804, the computer program is executed. The RAM 1804 is used for a temporary storage for input and output of data, a work memory for data communication, and a temporary storage for control of the devices. Examples of the external storage unit 1808 include a hard disk storage unit and a CD-ROM (compact disk-read only memory). The data stored in the external storage unit 1808 is held after the external storage unit 1808 is powered off.

By executing the computer program stored in the RAM 1804, the CPU 1802 performs the processes according to the first to fourth embodiments. The network interface 1805 is an interface for connecting the PC 111 to a network. The network interface 1805 receives and outputs signals and data from and to the radiation source 103, the flat panel detector 119, and the photograph button 115. Examples of the input unit 1806 include a keyboard and a mouse. A variety of instructions and data can be input through the input unit 1806. Examples of the output unit 1807 include a display and a printer. The output unit 1807 can display and print a subject image.

As described above, by executing the program, the PC 111 achieves the processes according to the first to fourth embodiments. In addition, medium for supplying the program to a computer (e.g., a computer-readable recording medium, such as a CD-ROM) that stores the program or a transmission medium (e.g., the Internet) that transmits the program can be an embodiment of the present invention.

Furthermore, a computer program product, such as a computer-readable recording medium, that stores the program can also be an embodiment of the present invention. The scope of the present invention encompasses the above-described program, recording medium, transmission medium, and computer program product. Examples of the recording medium include a flexible disk, a hard disk, an optical disk, a magnetooptical disk, a CD-ROM, a magnetic tape, a nonvolatile memory card, and a ROM.

As described above, according to the first to fourth embodiments, after a photoelectric conversion element is irradiated with a light ray having no image information in advance, the photoelectric conversion element is irradiated with a light ray again at an appropriate timing determined using information from a detection unit of the radiation imaging system.

Thus, the dark current, image ghosting, and sensitivity of the imaging apparatus can be stabilized. In addition, the light emission time to the conversion elements can be reduced, and therefore, the power consumption and the heat generation of the light source can be reduced. Furthermore, the durability of the conversion elements can be increased.

According to the present invention, the flat panel detector 119 includes a conversion unit having a plurality of conversion elements arranged in a matrix, each including the conversion elements D1 to D3. The plurality of conversion elements are capable of converting a radiation ray to electric charge. Each of the conversion elements includes the wavelength converter 104 that converts a radiation ray into a light ray and a photoelectric conversion element that converts the converted light ray into electric charge. The photoelectric conversion element includes an amorphous semiconductor disposed on an insulating substrate. The light source 105 can emit light having a wavelength within a wavelength range that is detectable by the conversion unit. The control unit 107 controls the flat panel detector 119 and the light source 105. More specifically, in an input step, the control unit 107 receives a signal from the flat panel detector 119. In a control step, the control unit 107 controls light emission performed by the light source 105 on the basis of the received signal.

According to the present invention, the flat panel detector 119 includes the drive circuit 110, the readout circuit 108, and the image processing circuit 122. The drive circuit 110 controls the switching elements T11 to T33 of the pixels between a conductive state and a non-conductive state in order to output electrical signals based on the electric charge converted by the conversion elements to the signal wires M1 to M3 on a row-to-row basis. In this way, the drive circuit 110 controls the sensor panel 102. The readout circuit 108 reads electrical signals output to the signal wires M1 to M3, and converts the analog signals to a digital image signal. The image processing circuit 122 performs signal processing on the converted digital image signal.

According to the first embodiment, the control unit 107 compares a dark output signal acquired from the flat panel detector 119 at predetermined intervals with a reference value. If the dark output signal is less than the reference value, the control unit 107 controls the light source 105 to emit light.

According to the second embodiment, the control unit 107 includes the timer 106. The timer 106 prestores a period of time from when the flat panel detector 119 is irradiated with the light emitted from the light source 105 until the dark output signal output from the flat panel detector 119 becomes less than the reference value. When the time period set in the timer 106 has elapsed, the control unit 107 controls the light source 105 to emit light.

According to the third embodiment, the subject detection sensor 116 detects the presence of a subject and outputs a subject detection signal. The control unit 107 controls the light source 105 to emit light on the basis of at least the signal output from the flat panel detector 119 and the subject detection signal output from the subject detection sensor 116.

According to the fourth embodiment, the position detection sensor 117 detects whether the flat panel detector 119 is disposed at a position where the flat panel detector 119 can perform a photographing operation and outputs a position detection signal. The control unit 107 controls the light source 105 to emit light on the basis of at least the signal output from the flat panel detector 119 and the position detection signal output from the position detection sensor 117.

While the present invention has been described with reference to the first to fourth embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Application No. 2007-064124 filed Mar. 13, 2007 and No. 2008-032200 filed Feb. 13, 2008, which are hereby incorporated by reference herein in their entirety.

What is claimed is:

1. A radiation imaging apparatus comprising:
a flat panel detector including a conversion unit, said conversion unit including a plurality of pixels arranged in a matrix, each of said pixels including a conversion element capable of converting a radiation ray into electric charge;
a light source capable of emitting light to said conversion unit; and
a control unit configured to control said flat panel detector and said light source, said control unit controlling the emission of light performed by said light source on the basis of a dark-output value output from said flat panel detector, wherein the dark-output value is an output from said flat panel detector obtained in a dark state in which no radiation ray or light ray is input to said flat panel detector.

2. The radiation imaging apparatus according to claim 1, wherein said control unit compares a predetermined reference value with the dark-output value acquired from said flat panel detector at predetermined intervals and controls the emission of light performed by said light source on the basis of the comparison result.

3. The radiation imaging apparatus according to claim 2, wherein said control unit compares a predetermined reference value with the dark-output value acquired from said flat panel detector at predetermined intervals and controls said light source to emit light when the dark-output value is less than the reference value.

4. The radiation imaging apparatus according to claim 2, wherein said control unit includes a timer, and a period of time from when said light source starts emitting light to said flat panel detector until the dark-output value output from said flat panel detector is less than the reference value is set in said timer, and wherein said control unit controls said light source to emit light when the period of time set in said timer has elapsed.

5. The radiation imaging apparatus according to claim 4, further comprising:
a subject detection sensor configured to detect the presence of a subject and output a subject detection signal,
wherein said control unit controls the emission of light performed by said light source on the basis of at least a signal output from the timer, the subject detection signal output from said subject detection sensor, and the state of a radiation source.

6. The radiation imaging apparatus according to claim 4, further comprising:
a position detection sensor configured to detect whether said flat panel detector is disposed at a position at which a photographing operation is available and output a position detection signal,
wherein said control unit controls the emission of light performed by said light source on the basis of at least a signal output from the timer, the position detection signal output from said position detection sensor, and the state of a radiation source.

7. The radiation imaging apparatus according to claim 1, wherein said flat panel detector includes:
a drive circuit configured to output an electrical signal based on the electric charge converted by said conversion element to a signal wire;
a readout circuit configured to read out the electrical signal output to said signal wire and convert the electrical signal from an analog format to a digital format; and
a processing circuit configured to perform processing on the converted digital signal.

8. The radiation imaging apparatus according to claim 1, wherein said conversion element includes a wavelength converter that converts a radiation ray to a light ray and a photoelectric conversion element that converts the converted light ray to electric charge.

9. The radiation imaging apparatus according to claim 8, wherein said photoelectric conversion element includes an amorphous semiconductor disposed on an insulating substrate.

10. A radiation imaging system comprising:
said radiation imaging apparatus according to claim 1; and
a radiation source configured to radiate a radiation ray.

11. A method for controlling a radiation imaging apparatus, comprising the steps of:
receiving a dark-output value from a flat panel detector including a conversion unit, wherein the dark-output value is an output from the flat panel detector obtained in a dark state in which no radiation ray or light ray is input to the flat panel detector, the conversion unit including a plurality of pixels arranged in a matrix, each of the pixels including a conversion element capable of converting a radiation ray into electric charge; and
controlling a light source to emit light to the conversion unit on the basis of the received dark-output value.

12. A non-transitory computer-readable recording medium that stores a program for causing a computer to control a radiation imaging apparatus, the program comprising program code for causing the radiation imaging apparatus to execute:
the step of receiving a dark-output value from a flat panel detector including a conversion unit, wherein the dark-output value is an output from the flat panel detector obtained in a dark state in which no radiation ray or light ray is input to the flat panel detector, where the conversion unit includes a plurality of pixels arranged in a matrix and each of the pixels includes a conversion element capable of converting a radiation ray into electric charge; and
the step of controlling a light source to emit light to the conversion unit on the basis of the received dark-output value.

* * * * *